US008163501B2

(12) United States Patent
Targan et al.

(10) Patent No.: US 8,163,501 B2
(45) Date of Patent: *Apr. 24, 2012

(54) METHODS OF ASSESSING CROHN'S DISEASE PATIENT PHENOTYPE BY I2 SEROLOGIC RESPONSE

(75) Inventors: Stephen R. Targan, Santa Monica, CA (US); Eric A. Vasiliauskas, Manhattan Beach, CA (US); William S. Mow, Culver City, CA (US); Huiying Yang, Cerritos, CA (US); Phillip R. Fleshner, Beverly Hills, CA (US); Jerome I. Rotter, Los Angeles, CA (US)

(73) Assignee: Cedars-Sinai Medical, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/645,394

(22) Filed: Dec. 22, 2009

(65) Prior Publication Data
US 2010/0240077 A1    Sep. 23, 2010

Related U.S. Application Data

(63) Continuation of application No. 10/413,501, filed on Apr. 11, 2003, now Pat. No. 7,662,569.

(51) Int. Cl.
*G01N 33/53* (2006.01)
*G01N 33/542* (2006.01)
*G01N 33/00* (2006.01)
(52) U.S. Cl. .................. 435/7.1; 435/7.9; 435/7.92
(58) Field of Classification Search .................. None
See application file for complete search history.

(56) References Cited

U.S. PATENT DOCUMENTS

| | | | |
|---|---|---|---|
| 5,691,151 A | 11/1997 | Braun et al. | |
| 5,750,355 A | 5/1998 | Targan et al. | |
| 5,830,675 A | 11/1998 | Targan et al. | |
| 5,874,233 A | 2/1999 | Targan et al. | |
| 5,916,748 A | 6/1999 | Targan et al. | |
| 5,937,862 A | 8/1999 | Targan et al. | |
| 5,968,741 A | 10/1999 | Plevy et al. | |
| 6,074,835 A | 6/2000 | Braun et al. | |
| 6,309,643 B1 | 10/2001 | Braun et al. | |
| 7,138,237 B1 | 11/2006 | Targan et al. | |
| 7,662,569 B2 * | 2/2010 | Targan et al. | 435/7.1 |
| 2004/0053263 A1 | 3/2004 | Abreu et al. | |

FOREIGN PATENT DOCUMENTS

WO   WO 00/66067   11/2000
WO   WO 01/89361    5/2001

OTHER PUBLICATIONS

Vasiliauskas et a. 'Marker antibody expression stratifies Crohn's disease into immunologically homogeneous subgroups with distinct clinical characteristics.' Gut 47:487-496, 2000.*

Landers et al. 'Selected loss of tolerane evidenced by Crohn's Disease-Associated immune responses to auto- and microbial antigen.' Gastroenterology. 123(3):689-699, 2002.*
Dubinsky et al. 'Serum immune responses predict rapid disease progression among children with Crohn's Disease:immune responses predict disease progression.' Am. J. Gastroenterology 101:360-367, 2006.*
Abreu et al., "Mutations in NOD2 Are Associated with Fibrostenosing Disease in Patients with Crohn's Disease," Gastroenterology, 123:679-688, 2002.
Ahmad et al., "The Molecular Classification of the Clinical Manifestations of Crohn's Disease," Gastroenterology, 122:854-866, 2002.
Annese et al., "Familial expression of anti-*Saccharomyces cerevisiae* mannan antibodies in Crohn's disease and ulcerative colitis: a GISC study." Am. J. Gastroenterology 96: 2407-2412, 2001.
Arnott et al., "Sero-Reactivity to Microbial Components in Crohn's Disease is Associated with Disease Severity and Progression, But Not NOD2/CARD15 Genotype," Am. J. Gastroenterol., 99:2376-2384, 2004.
Cuthbert et al., "The contribution of NOD2 gene mutations to the risk and site of disease in inflammatory bowel disease." *Gastroenterology* 122: 867-874, 2002.
Dalwadi et at "The Crohn's Disease-Associated Bacterial Protein I2 Is a Novel Enteric T Cell Superantigen," Immunity, 15:149-158, 2001.
Elson, "Genes, microbes, and T cells—new therapeutic targets in Crohn's disease." *New Engl. J. Med.* 346: 614-616, 2002.
Gasche et al., "A Simple Classification of Crohn's Disease: Report of the Working Party for the World Congresses of Gastroenterology, Vienna 1998," Inflamm. Bowel Dis., 6:8-15, 2000.
Greenstein et al., "Perforating and Non-Perforating Indications for Repeated Operations in Crohn's Disease: Evidence for Two Clinical Forms," Gut, 29:588-592, 1988.
Hampe et al., "Association between Insertion Mutation in NOD2 Gene and Crohn's Disease in German and British Populations," Lancet, 357:1925-1928, 2001.
Helio et al., "CARD15/NOD2 gene variants are associated with familially occurring and complicated forms of Crohn's disease." *Gut* 52: 558-562, 2003.

(Continued)

*Primary Examiner* — Nora Rooney
(74) *Attorney, Agent, or Firm* — Kilpatrick Townsend & Stockton LLP

(57) ABSTRACT

The invention provides a method of diagnosing or predicting susceptibility to a clinical subtype of Crohn's disease in a subject having Crohn's disease by determining the presence or absence of IgA anti-I2 antibodies in the subject, where the presence of the IgA anti-I2 antibodies indicates that the subject has a clinical subtype of Crohn's disease. In one embodiment, a method of the invention is practiced by further determining the presence or absence in the subject of a NOD2 variant, anti-*Saccharomyces cerevisiae* antibodies (ASCA), IgA anti-OmpC antibodies, or perinuclear anti-neutrophil cytoplasmic antibodies (pANCA). The methods of the invention can be used to diagnose or predict susceptibility to a clinical subtype of Crohn's disease, for example, a fibrostenotic subtype, a subtype characterized by the need for small bowel surgery, or a subtype characterized by the absence of features of ulcerative colitis.

32 Claims, 7 Drawing Sheets

OTHER PUBLICATIONS

Hugot et al., "Association of NOD2 Leucine-Rich Repeat Variants with Susceptibility to Crohn's Disease," Nature, 411:599-603, 2001.

Hugot et al., "Mapping of Susceptibility Locus for Crohn's Disease on Chromosome 16," Nature, 379:821-823, 1996.

Inohara et al., "Host recognition of bacterial muramyl dipeptide mediated through NOD2. Implications for Crohn's disease." *J. Biol. Chem.* 278: 5509-5512, 2003.

Kuby et al., Immunology, 5th Edition, WH Freeman, Publisher, pp. 62-67, 2003.

Landers et al., "IgA Serum Antibody Reactivity with I2, A Novel Crohn's Disease Marker: Anti-I2 Level Is Independent from ASCA and ANCA Levels, Even Though IgA ASCA Positivity Is Correlated with Anti-I2 Positivity," Gastroenterology, 118(4):Suppl. 2, Part 1, A348, 2000.

Lesage et al., "CARD15/NOD2 Mutational Analysis and Genotype-Phenotype Correlation in 612 Patients with Inflammatory Bowel Disease," Am. J. Hum. Genet., 70:845-857, 2002.

Louis et al., "Early development of stricturing or penetrating pattern in Crohn's disease is influenced by disease location, number of flares, and smoking but not by NOD2/CARD15 genotype." *Gut* 52: 552-557, 2003.

Mow et al., "Antibodies against the Crohn's disease (CD)-associated bacterial sequence I2 (anti-I2) are an independent marker of fibrostenosing CD." *Gastroenterology* 124(4 Supplel): A2 Abstract #26, Apr. 2003.

Mow, et al., "Association of Antibody Responses to Microbial Antigens and Complications of Small Bowel Crohn's Disease." *Gastroenterology* 126: 414-424, 2004.

Ogura et al., "A Frameshift Mutation in NOD2 Associated with Susceptibility to Crohn's Disease," Nature, 411:603-606, 2001.

Papp et al., "Seroreactivity to Microbial Components in Crohn's Disease is Associated with Ileal Involvement, Noninflammatory Disease Behavior and NOD2/CARD15 Genotype, But Not with Risk for Surgery in a Hungarian Cohort of IBD Patients," Inflam. Bowel Dis., 13(8):984-992, Aug. 2007.

Quinton et al., "Anti-*Saccharomyces cerevisiae* mannan antibodies combined with antineutrophil cytoplasmic autoantibodies in inflammatory bowel disease: prevalence and diagnostic role." *Gut* 42: 788-791, 1998.

Radlmayr et al., "The c-insertion mutation of the NOD2 gene is associated with fistulizing and fibrostenotic phenotypes in Crohn's disease." *Gastroenterology* 122: 2091-2092, 2002.

Saxon et al., "A Distinct Subset of Antineutrophil Cytoplasmic Antibodies is Associated with Inflammatory Bowel Disease," J. Allergy Clin. Immunol., 86:202-210, 1990.

Sendid et al., "Specific Antibody Response to Oligomannosidic Epitopes in Crohn's Disease," Clin. Diagn. Lab Immunol., 3:219-226, 1996.

Sugimura et al., "A Novel NOD2/CARD15 Haplotype Conferring Risk for Crohn's Disease in Ashkenazi Jews," Am. J. Hum. Genet., 72:509-518, 2003.

Sutton et al., "Familial expression of Anti-*Saccharomyces cerevisiae* mannan antibodies in affected and unaffected relatives of patients with Crohn's disease." *Gut* 46: 58-63, 2000.

Sutton et al., "Identification of a Novel Bacterial Sequence Associated with Crohn's Disease," Gastroenterology, 119:23-31, 2000.

Targan et al., Gastroenterology, vol. 122, No. 4, Suppl., p. A-177, No. S1176, 2002.

Vasiliauskas et al., "Perinuclear Antineutrophil Cytoplasmic Antibodies in Patients with Crohn's Disease Define a Subclinical Subgroup," Gastroenterology, 110:1810-1819, 1996.

Wei et al., "Pseudomonas fluorescens Encodes the Crohn's Disease-Associated I2 Sequence and T-Cell Superantigen," Infect. Immun., 70:6567-6575, 2002.

\* cited by examiner

```
A   GAT CTG GCC AGC GCC GTG GGC ATC CAG TCC CCC AGC ATC TTT CAT CAC TTT AAG AGC AAG
▲   D   L   A   S   A   V   G   I   Q   S   P   S   I   F   H   H   F   K   S   K

GAT GAG ATA TTG CGT GCC GTG ATG GAG GAA ACC ATC CAT TAC AAC ACG GCG ATG ATG CGC
▲   D   E   I   L   R   A   V   M   E   E   T   I   H   Y   N   T   A   M   M   R

GCT TCA CTG GAG GAG CCG AGC ACG GTG CGC GAA CCG CTG ATC CGC TCC GAG
▲   A   S   L   E   E   A   S   T   V   R   E   P   L   I   R   C   E

TTG CAG TCG ATC ATG GGC GCG AGT CGC GAG GCC ATG GCG GTG CTG GTC TAC GAA TGG CGC
▲   L   Q   S   I   M   G   A   S   R   E   A   M   A   V   L   V   Y   E   W   R

TCG CFG TCG GOC GAA OCC CAG GCG CAC GTG CTG GOC CTG TAT GAG CAG ATC T
▲   S   L   S   A   E   O   A   H   V   L   A   L   R   D   Y   E   O   I
```

```
5' ACCTTCAGAT CACAGCAGCC TTCCTGGCAG GGCTGTTGTC CCGGGAGCAC    50
3' TGGAAGTCTA GTGTCGTCGG AAGGACCGTC CCGACAACAG GGCCCTCGTG

TGGGGCCTCC TGGCTGAGTG CCAGACATCT GAGAAGGCCC tgctccgggg   100
   ACCCCGGACG ACCGACTCAC GGTCTGTAGA CTCTTCCGGG acgaggccgc ccaGGCTGTG CCCGCCTGGT GTCTGGCCCG CAGCCTCCGC AAGCACTTCC   150
   ggtCCGACAC GGGCGGACCA CAGACCGGGC GTCGGAGGCG TTCGTGAAGG ACTCCATCCC GCCAGCTGCA CCGGGTGAGG CCAAGAGCGT GCATGCCATG   200
   TGAGGTAGGG CGGTCGACCT GGCCCACTCC GGTTCTCGCA CGTACGGTAC CCCGGGTTCA TCTGGCTCAT CCGGAGCCTG TACGAGATGC AGGAGGAGCG   250
   GGGCCCAAGT AGACCGAGTA GGCCTCGGAC ATGCTCTACG TCCTCCTCGC GCTGGCTCGG AAGGCTGCAC GTGGCCTGAA TGTTGGGCAC CTCAAGTTGA   300
   CGACCGAGCC TTCCGACGTG CACCGGACTT ACAACCCGTG GAGTTCAACT CATTTTGCAG TGTGGGCCCC ACTGAGTGTG CTGCCCTGGC CTTTGTGCTG   350
   GTAAAACGTC ACACCCGGGG TGACTCACAC GACGGGACCG GAAACACGAC CAGCACCTCC GGCGGCCCGT GGCCCTGCAG GTGGACTACA ACTCTGTGGG   400
   GTCGTGGAGG CCGCCGGGCA CCGGGACGTC CACCTGATGT TGAGACACCC TGACATTGGC GTGGAGCAGC TGCTGCCTTG CCTTGGTGTC TGCAAGGCTC   450
   ACTGTAACCG CACCTCGTCG ACGACGGAAC GGAACCACAG ACGTTCCGAG TGTAGTGAGT GTTACTGGGC ATTGCTGTTC AGGTATGGGG GAGC 3' SEQ ID NO3  494
   ACATCACTCA CAATGACCCG TAACGACAAG TCCATACCCC CTCG 5' SEQ ID NO4
```

```
5' ATCAAAACCC TGAGAGGACA AGGGACATTT CCAAGTCACC CAGAAAGACT      50
3' TAGTTTTGGG ACTCTCCTGT TCCCTGTAAA GGTTCAGTGG GTCTTTCTGA

CGAGTGTCCT CTCTTGAAAT CCAATGGTCT TTTTTCCTTA CTCCATTGCC     100
   GCTCACAGGA GAGAACTTTA GGTTACCAGA AAAAGGAAT  GAGGTAACGG

TAACATTGTG GGGTAGAAAT AAAGTTCAAA GACCTTCAGA ACTGGCCCCA     150
   ATTGTAACAC CCCATCTTTA TTTCAAGTTT CTGGAAGTCT TGACCGGGGT

GCTCCTCCCT CTTCACCTGA TCTCCCCAAG AAAACTGCAG GATAGACTCT    200
   CGAGGAGGGA GAAGTGGACT AGAGGGGTTC TTTTGACGTC CTATCTGAGA

GAAGCTTACC TGAGCCACCT CAAGCTCTGG TGATCACCCA AGGCTTCAGC    250
   CTTCGAATGG ACTCGGTGGA GTTCGAGACC ACTAGTGGGT TCCGAAGTCG

CAGGGCCTGG GCCCCCTCGT CACCCActct gttgccccag aaTCTGAAAA    300
   GTCCCGGACC CGGGGGAGCA GTGGGTgaga caacggggtc ttAGACTTTT GGCCAAAAGA GTCAACAGAC AGTGTCAGTG AGTACCTGAT ATGTGTTCTA    350
   CCGGTTTTCT CAGTTGTCTG TCACAGTCAC TCATGGACTA TACACAAGAT GACATGAACT AACAGTCCTC CTCCCTCTGC AGTCCCAGCC AGAGGGGCAG    400
   CTGTACTTGA TTGTCAGGAG GAGGGAGACG TCAGGGTCGG TCTCCCCGTC GACCACTCAA TCCCAGAGTG GCCTCACTGG GGCTCCTGGT CCCAGCAAAG    450
   CTGGTGAGTT AGGGTCTCAC CGGAGTGACC CCGAGGACCA GGGTCGTTTC TGGACCTGCC TCCATCTTTT GGGTGGGATG GCCAAACTTA ACCCAAGAGT    500
   ACCTGGACGG AGGTAGAAAA CCCACCCTAC CGGTTTGAAT TGGGTTCTCA TTTCAGTGGC TTTACATTAC AGACTTAGAG AATAGTAGAG3' -SEQ ID NO 5   540
    AAAGTCACCG AAATGTAATG TCTGAATCTC TTATCATCTC5' -SEQ ID NO 6
```

```
5' TTTAAAAATG AAATCATTGC TCCCTACTTA AAGAGGTAAA GACTTCTTTC    50
3' AAATTTTTAC TTTAGTAACG AGGGATGAAT TTCTCCATTT CTGAAGAAAG

TTAGACAGAG AATCAGATCC TTCACATGCA GAATCATTCT CACTGAATGT   100
   AATCTGTCTC TTAGTCTAGG AAGTGTACGT CTTAGTAAGA GTGACTTACA

CAGAATCAGA AGGGATCCTC AAAATTCTGC CATTCCTCTC TCCCGTCACC   150
   GTCTTAGTCT TCCCTAGGAG TTTTAAGACG GTAAGGAGAG AGGGCAGTGG

CCATTTTACA GATAGAAAAA CTGAGGTTCG GAGAGCTAAA ACAGGCCTGC   200
   GGTAAAATGT CTATCTTTTT GACTCCAAGC CTCTCGATTT TGTCCGGACG

CCAGGGGCCT TACCAGACTT CCAGGATGGT GTCATIcctt tcaagggcc    250
   GGTCCCCGGA ATGGTCTGAA GGTCCTACCA CAGTAAggaa agttcccggg tgcAGGAGGG CTTCTGCCCC TAGGTAGGTG ATGCAGTTAT TGGACAACCT   300
   acgTCCTCCC GAAGACGGGG ATCCATCCAC TACGTCAATA ACCTGTTGGA GGAAAAGAAG ATACAATGGT GAGCTTCAAG GATTCTTGGT TTTCCTCTTG   350
   CCTTTTCTTC TATGTTACCA CTCGAAGTTC CTAAGAACCA AAAGGAGAAC AAACTGTCCA GTTAAAGAGA CTGCAGGAGT TAGCCAGTCT ACTGAAGCCC   400
   TTTGACAGGT CAATTTCTCT GACGTCCTCA ATCGGTCAGA TGACTTCGGG ACCTGTCCCT TAGACACATC CTGCTCATGT CTGAGATTCC CAATGAGCTC   450
   TGGACAGGGA ATCTGTGTAG GACGAGTACA GACTCTAAGG GTTACTCGAG ATCAACAAAG GCTCAGTACC ATCAGTGAAA TGTAACCGTC TCTCTTCCAT   500
   TAGTTGTTTC CGAGTCATGG TAGTCACTTT ACATTGGCAG AGAGAAGGTA TCACTAGATG AGTTTATCAA ATTAAGTAGC CACTCCCCTTA G3' -SEQ ID NO 7   541
     AGTGATCTAC TCAAATAGTT TAATTCATCG GTGAGGGAAT C5' -SEQ ID NO 8
```

FIG. 2D

```
atgaaagtta aagtactgtc cctcctggtc ccagctctgc tggtagcagg cgcagcaaac cgcagcaaag gctgctgaag tttacaacaa
agacggcaac aaattagatc tgtacggtaa agtagacggc ctgcactatt tctctgacaa caaagatgta gatggcgacc
agacctacat gcgtcttggc ttcaaaggtg aaactcaggt tactgaccag ctgaccggtt acggccagtg ggaatatcag
atccagggca acagcgctga aaacgaaaac aactcctgga cccgtgtgtc attcgcaggt ctgaaattcc
aggatgtggg ttctttcgac tacggtcgta actacgcgcg tgtttatgac gtaacttcct ggaccgacgt actgccagaa
ttcggtggtg acacctacgg ttctgacaac ttcatgcagc agcgttgtaa cggcttcgcg acctaccgta acactgactt
cttcggtctg gttgacggcc tgaactttgc tgttcagtac cagggtaaaa acggcaaccc atctggtgaa ggctttacta
gtgcgtaac cgtgacgcac tgcgtcaaaa cggcgacggc gtcggcggtt ctatcactta tgattacgaa
ggtttcgta tcggtggtgc gatctccagc ctgatgctca gaacaccgct gcttacatcg gtaacggcga
ccgtgctgaa acctacggta gtggttcc ctgggttggg cgaacaaagc acagaacttc gaagctgttg ctcagtacca gttcgacttc
acgcaactcg cgtaggttcc cgtccctggc ttacctgcag tctaaaggta aaaacctggg tcgtgctac gacgacgaag atatcctgaa
ggtctgcgtc cgtggtgcta cctactactt caacaaaaac atgtccacct acgttgacta caaaatcaac ctgctggacg
atatgttgat gttggtgcta cctactactt caacaaaaac atgtccacct acgttgacta caaaatcaac ctgctggacg
acaaccagtt cactcgtgac gctggcatca catcgtagct ctggtctgg tttaccagtt c SEQ ID NO:9
```

FIG. 3A

```
MKVKVLSLLVPALLVAGAANAAEVYNKDGNKLDLYGKVDGLHYFSDNKDVDGDQTY
MRLGFKGETQVTDQLTGYGQWEYQIQGNSAENENNSWTRVAFAGLKFQDVGSFDYGR
NYGVVYDVTSWTDVLPEFGGDTYGSDNFMQQRGNGFATYRNTDFFGLVDGLNFAVQY
QGKNGNPSGEGFTSGVTNNGRDALRQNGDGVGGSITYDYEGFGIGGAISSSKRTDAQNT
AAYIGNGDRAETYTGGLKYDANNIYLAAQYTQTYNATRVGSLGWANKAQNFEAVAQY
QFDFGLRPSLAYLQSKGKNLGRGYDDEDILKYVDVGATYYFNKNMSTYVDYKINLLDD
NQFTRDAGINTDNIVALGLVYQF
```

SEQ ID NO:10

FIG. 3B

METHODS OF ASSESSING CROHN'S DISEASE PATIENT PHENOTYPE BY I2 SEROLOGIC RESPONSE

This invention was made with government support under grant number DK 46763 awarded by the National Institutes of Health. The United States Government has certain rights in this invention.

BACKGROUND OF THE INVENTION

This invention relates generally to the fields of diagnostics and autoimmune disease and, more specifically, to serologic and genetic methods for diagnosing clinical subtypes of Crohn's disease.

Inflammatory bowel disease (IBD) is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. Onset of IBD is predominantly in young adulthood with diarrhea, abdominal pain, and fever the three most common presenting symptoms. The diarrhea may range from mild to severe, and anemia and weight loss are additional common signs of IBD. Of all patients with IBD, ten percent to fifteen percent will require surgery over a ten year period. In addition, patients with IBD are at increased risk for the development of intestinal cancer. Reports of an increasing occurrence of psychological problems, including anxiety and depression, are perhaps not surprising symptoms of what is often a debilitating disease that strikes people in the prime of life.

Unfortunately, the available therapies for inflammatory bowel disease are few, and both diagnosis and treatment have been hampered by a lack of knowledge regarding the etiology of the disease. However, it is thought that a combination of genetic factors, exogenous triggers and endogenous microflora can contribute to the immune-mediated damage to the intestinal mucosa seen in inflammatory bowel disease. In Crohn's disease, bacteria have been implicated in initiation and progression of the disease: the intestinal inflammation in Crohn's disease is notable for its frequent responsiveness to antibiotics and susceptibility to bacterial fecal flow. Common intestinal colonists and novel pathogens have been implicated in Crohn's by direct detection or by disease associated anti-microbial immune responses. Furthermore, in many genetically susceptible animal models of chronic colitis, lumenal micro-organisms are a necessary cofactor for disease; animals housed in a germ-free environment do not develop colitis.

It is increasingly apparent that Crohn's disease is a classification representing a number of heterogeneous disease subtypes that affect the gastrointestinal tract and produce similar symptoms. Both environmental and genetic factors likely contribute to the etiology of such disease subtypes. Patients with Crohn's disease can be classified, for example, into subtypes based on the presence of fibrostenotic disease, internal-perforating disease, perianal fistulizing disease or ulcerative colitis-like disease according to previously described criteria. The extensive and often protracted clinical testing required to determine Crohn's disease subtypes may delay optimal treatment and involves invasive procedures such as endoscopy.

Identification of serologic and genetic markers which are closely associated with a clinical subtype of Crohn's disease would provide the basis for novel diagnostic tests and eliminate or reduce the need for the battery of laboratory, radiological, and endoscopic evaluations typically required to determine disease subtype. The availability of methods for diagnosing clinical subtypes of Crohn's disease would represent a major clinical advance that would aid in the therapeutic management of Crohn's disease and would further lay the groundwork for the design of treatment modalities which are specific to a particular disease subtype. Such methods can reduce costs associated with treatment of unresponsive disease subtypes and eliminate the disappointment of those needlessly undergoing ineffective therapy. In particular, a reliable genetic test for the fibrostenotic subtype of Crohn's disease would be highly prized as a non-invasive method for the early diagnosis of this disease subtype and would also be useful for predicting susceptibility to the fibrostenotic subtype of Crohn's disease in asymptomatic individuals, making prophylactic therapy possible. The present invention satisfies this need and provides related advantages as well.

SUMMARY OF THE INVENTION

The invention provides a method of diagnosing or predicting susceptibility to a clinical subtype of Crohn's disease in a subject having Crohn's disease by determining the presence or absence of IgA anti-I2 antibodies do the subject, where the presence of the IgA anti-I2 antibodies indicates that the subject has a clinical subtype of Crohn's disease. In one embodiment, a method of the invention is practiced by further determining the presence or absence in the subject of a NOD2 variant, anti-*Saccharomyces cerevisiae* antibodies (ASCA), IgA anti-OmpC antibodies, or perinuclear anti-neutrophil cytoplasmic antibodies (pANCA). The methods of the invention can be used to diagnose or predict susceptibility to a clinical subtype of Crohn's disease, for example, a fibrostenotic subtype, a subtype characterized by the need for small bowel surgery, or a subtype characterized by the absence of features of ulcerative colitis.

BRIEF DESCRIPTION OF THE DRAWINGS

FIG. 1 shows an I2 nucleotide sequence (SEQ ID NO: 1) and predicted amino acid sequence (SEQ ID NO: 2)

FIG. 2B shows the nucleotide sequence of the NOD2 gene surrounding the R702W NOD2 variant. The top strand is labeled as SEQ ID NO:3 and the bottom strand is labeled as SEQ ID NO:4. Nucleotide sequences which can be used as primers for PCR amplification are indicated. FIG. 2C shows the nucleotide sequence of the NOD2 gene surrounding the G908R NOD2 variant. The top strand is labeled as SEQ ID NO:5 and the bottom strand is labeled as SEQ ID NO:6. Nucleotide sequences which can be used as primers for PCR amplification are indicated. FIG. 2D shows the nucleotide sequence of the NOD2 gene surrounding the 1007fs NOD2 variant. The top strand is labeled as SEQ ID NO:7 and the bottom strand is labeled as SEQ ID NO:8. Nucleotide sequences which can be used as primers for PCR amplification are indicated. In FIGS. 2B, C and D, the position of a nucleotide sequence which can be used as a probe in an allelic discrimination assay is boxed and the position of the polymorphic site is underlined.

FIG. 3A shows the nucleotide sequence (SEQ ID NO:9) of an *E. coli* outer membrane protein c (OmpC) precursor and FIG. 3B shows the corresponding amino acid sequence (SEQ ID NO:10).

DETAILED DESCRIPTION OF THE INVENTION

Figure 2A:
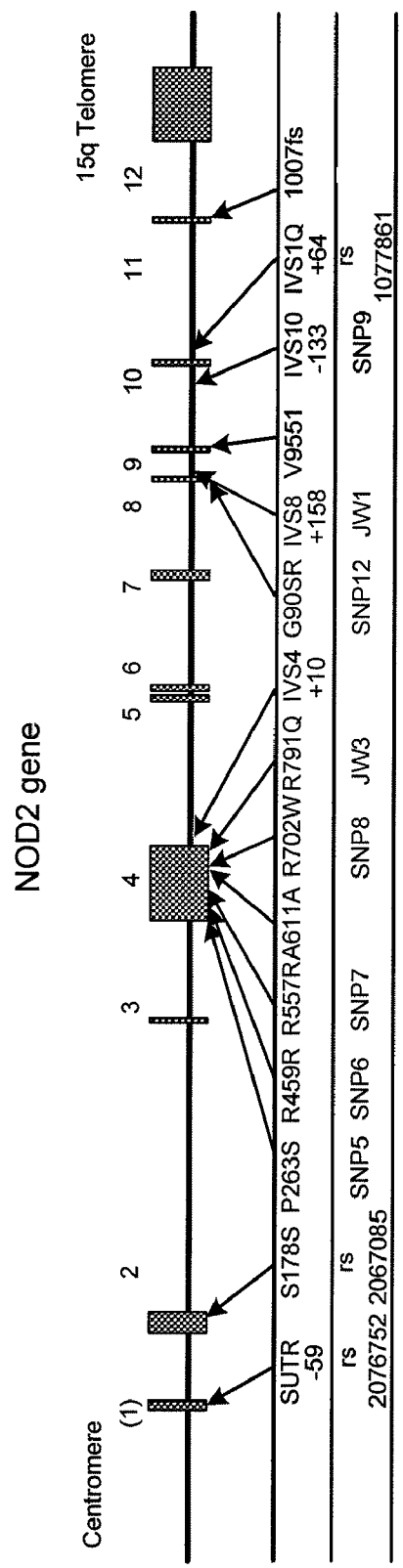
FIG. 2A shows an illustration of the NOD2 gene locus. The location of selected NOD2 variants is indicated.

The present invention is directed to the exciting discovery of serologic and genetic markers that are closely associated with the fibrostenotic subtype of Crohn's disease. These markers can be used to diagnose or predict susceptibility to the fibrostenotic subtype of Crohn's disease in a subject having Crohn's disease.

As disclosed herein, ELISAs for IgA anti-I2 antibodies and anti-*Saccharomyces cerevisiae* antibodies (ASCA) were performed on 258 Crohn's disease patients (Examples II and III, respectively). In addition, genotyping was performed on these patients for three Crohn's disease associated variants of the NOD2 gene, R702W, G908R, and 1007fs, using the Taqman® MGB system as described in Example IV.

As disclosed in herein, IgA antibodies to I2 were present in 56.5% of the Crohn's disease patients in the study (see Example I). Patients expressing IgA anti-I2 antibodies were significantly more likely to have a fibrostenotic subtype of Crohn's disease than those not expressing IgA anti-I2 antibodies (71.4% vs. 43.3%, p<0.001) and significantly more likely to require small bowel surgery (66.7% vs. 37.1%, p<0.001). In addition, IgA anti-I2 antibody expression was negatively associated with ulcerative colitis-like Crohn's disease (20.6% vs. 41.24%, p<0.001). Quartile analyses revealed that higher levels of IgA anti-I2 antibodies were more strongly associated with the fibrostenotic subtype of Crohn's disease (p for the trend <0.001) and small bowel involvement (p=0.023), and inversely associated with ulcerative colitis-like Crohn's disease (p=0.005) compared to lower levels of IgA anti-I2 antibodies. In addition, as disclosed in Example I, conditional analysis performed on NOD2 variants and ASCA indicated that IgA anti-I2 antibodies were independently associated with the fibrostenotic subtype (p=0.001 and p=0.005, respectively). Similarly, IgA anti-I2 was independently associated with small bowel surgery when conditioned on NOD2 variation (p=0.001) or ASCA (p=0.002). These results indicate that the presence of IgA anti-I2 antibodies can be used to diagnose or predict susceptibility to a clinical subtype of Crohn's disease, such as the fibrostenotic subtype, in a subject having Crohn's disease.

As further disclosed in Example I, patients with all three markers, IgA anti-I2 antibodies, one of the three NOD2 variants, and ASCA showed the greatest risk of the fibrostenotic subtype of Crohn's disease (82%, odds ratio=9.7; p<0.000001), compared with patients with two markers (74%, odds ratio=6.0), one marker (48%, odds ratio=1.9), or none of these markers (33%, odds ratio=reference group). These results indicate that the presence of IgA anti-I2 antibodies in combination with the presence of other markers can be used to diagnose or predict susceptibility to a fibrostenotic subtype Crohn's disease in a patient having Crohn's disease.

Based on these findings, the present invention provides a method of diagnosing or predicting susceptibility to a clinical subtype of Crohn's disease in a subject having Crohn's disease by determining the presence or absence of IgA anti-I2 antibodies in the subject, where the presence of the IgA anti-I2 antibodies indicates that the subject has a clinical subtype of Crohn's disease. The methods of the invention can be advantageous in that they are noninvasive and can be conveniently practiced, for example, with a blood sample from the subject. The methods of the invention can be used to quickly, easily and reliably diagnose or predict susceptibility to a clinical subtype of Crohn's disease, for example, a fibrostenotic subtype, a subtype characterized by the need for small bowel surgery, or a subtype characterized by the absence of features of ulcerative colitis, as described herein. The methods of the invention can also be advantageous in that they can be useful for predicting how a subject will respond to a certain therapy.

In one embodiment, a method of the invention is practiced by determining the presence or absence of IgA anti-I2 antibodies in a subject having Crohn's disease and further determining the presence or absence in the subject of a NOD2 variant, anti-*Saccharomyces cerevisiae* antibodies (ASCA), IgA anti-OmpC antibodies, or perinuclear anti-neutrophil cytoplasmic antibodies (pANCA). Such a NOD2 variant can be, for example, R702W, G908R, or 1007fs. In a further embodiment, determining the presence or absence of IgA anti-I2 antibodies in the subject is practiced by contacting a sample from the subject with an I2 antigen, or immunoreactive fragment thereof, under conditions suitable to form a complex of I2 antigen, or immunoreactive fragment thereof, and antibody against the I2 antigen; contacting the complex with a labeled secondary antibody; and detecting the presence or absence of the complex, where the presence of the complex indicates the presence of the anti-I2 antibodies in the subject.

The invention also provides a method of diagnosing or predicting susceptibility to a fibrostenotic subtype of Crohn's disease by determining the presence or absence of IgA anti-I2 antibodies in a subject having Crohn's disease, where the presence of IgA anti-I2 antibodies indicates that the subject has the fibrostenotic subtype of Crohn's disease. In one embodiment, a method of the invention is practiced by further determining the presence or absence in the subject of one or more of the following fibrostenotic markers: a NOD2 variant, anti-*Saccharomyces cerevisiae* antibodies (ASCA), or IgA anti-OmpC antibodies. Such a NOD2 variant can be, for example, R702W, G908R, or 1007fs NOD2 variant. In a further embodiment, a method of the invention is practiced by determining the presence or absence of anti-I2 antibodies, a NOD2 variant and ASCA. In yet a further embodiment, determining the presence or absence of IgA anti-I2 antibodies in the subject is practiced by contacting a sample from the subject with an I2 antigen, or immunoreactive fragment thereof, under conditions suitable to form a complex of I2 antigen, or immunoreactive fragment thereof, and antibody against the I2 antigen; contacting the complex with a labeled secondary antibody; and detecting the presence or absence of the complex, where the presence of the complex indicates the presence of the IgA anti-I2 antibodies in the subject.

In one embodiment, a method of the invention is practiced by determining the presence or absence in the subject of IgA anti-I2 antibodies and further determining the presence or absence of a NOD2 variant, where the presence of IgA anti-I2 antibodies and the presence of a NOD2 variant in the subject indicates that the subject has the fibrostenotic subtype of Crohn's disease. In a related embodiment, the combined presence of the IgA anti-I2 antibodies and the NOD2 variant in the subject is associated with the fibrostenotic subtype of Crohn's disease with an odds ratio of at least 6. In another embodiment, the invention is practiced by determining the presence or absence of IgA anti-I2 antibodies and further determining the presence or absence of ASCA in the subject, where the presence of the IgA anti-I2 antibodies and the presence of ASCA in the subject indicates that the subject has the fibrostenotic subtype of Crohn's disease. In a related embodiment, the combined presence of the anti-I2 antibodies and ASCA in the subject is associated with the fibrostenotic subtype of Crohn's disease with an odds ratio of at least 6. In a further embodiment, the invention is practiced by determining the presence or absence of IgA anti-I2 antibodies and further determining the presence or absence of a NOD2 variant and ASCA in the subject, where the combined presence of IgA anti-I2 antibodies, the NOD2 variant, and ASCA in the subject indicates that the subject has the fibrostenotic subtype of Crohn's disease. In a related embodiment, the combined presence of the anti-I2 antibodies, the NOD2 variant, and ASCA in the subject is associated with the fibrostenotic subtype of Crohn's disease with an odds ratio of at least 9.

The methods of the invention relate to the diagnosis and treatment of Crohn's disease (regional enteritis), which is a disease of chronic inflammation that can involve any part of the gastrointestinal tract. Commonly the distal portion of the small intestine (ileum) and cecum are affected. In other cases, the disease is confined to the small intestine, colon or anorectal region. Crohn's disease occasionally involves the duodenum and stomach, and more rarely the esophagus and oral cavity.

The variable clinical manifestations of Crohn's disease are, in part, a result of the varying anatomic localization of the disease. The most frequent symptoms of Crohn's disease are abdominal pain, diarrhea and recurrent fever. Crohn's disease is commonly associated with intestinal obstruction or fistula, which is an abnormal passage, for example, between diseased loops of bowel. Crohn's disease also may include complications such as inflammation of the eye, joints and skin; liver disease; kidney stones or amyloidosis. In addition, Crohn's disease is associated with an increased risk of intestinal cancer.

Several features are characteristic of the pathology of Crohn's disease. The inflammation associated with Crohn's disease, known as transmural inflammation, involves all layers of the bowel wall. Thickening and edema, for example, typically also appear throughout the bowel wall, with fibrosis also present in long-standing disease. The inflammation characteristic of Crohn's disease also is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of Crohn's disease.

A hallmark of Crohn's disease is the presence of discrete aggregations of inflammatory cells, known as granulomas, which are generally found in the submucosa. Some Crohn's disease cases display the typical discrete granulomas, while others show a diffuse granulomatous reaction or nonspecific transmural inflammation. As a result, the presence of discrete granulomas is indicative of Crohn's disease, although the absence of granulomas also is consistent with the disease. Thus, transmural or discontinuous inflammation, rather than the presence of granulomas, is a preferred diagnostic indicator of Crohn's disease (Rubin and Farber, *Pathology* (Second Edition) Philadelphia: J.B. Lippincott Company (1994)).

In contrast to ulcerative colitis, which is characterized by a continuous inflammation of the colon that usually is more severe distally than proximally, Crohn's disease is a patchy disease with frequent sparing of the rectum. Furthermore, the inflammation in Crohn's disease is distinct from the superficial inflammation seen in ulcerative colitis, which is usually limited to the mucosal layer and characterized by an acute inflammatory infiltrate with neutrophils and crypt abscesses. Instead, Crohn's disease affects the entire thickness of the bowel wall with granulomas often, although not always, present. Furthermore, involvement of the terminal ileum, a cobblestone-like appearance, discrete ulcers or fistula's suggest. Crohn's disease.

The diagnostic methods of the invention are practiced in a subject having Crohn's disease. As used herein, the term "subject" means any animal, such as a human or other mammal, capable of having Crohn's disease. A subject having Crohn's disease can have one or more symptoms of Crohn's disease or can be asymptomatic, having been previously diagnosed as having Crohn's, disease by one or more well established criteria. The methods of the invention can be useful, for example, for diagnosing a subtype of Crohn's disease in a subject with one or more symptoms of Crohn's disease. In one embodiment, the methods of the invention are used to determine the presence or absence of the fibrostenotic subtype of Crohn's disease in a subject known to have Crohn's disease. One skilled in the art understands that the methods of the invention also can be practiced in an individual not yet diagnosed as having Crohn's disease, for example, an individual at risk for having Crohn's disease. Such an individual can be, for example, genetically related to a subject with Crohn's disease or can belong to a population that is known to be at increased risk for having Crohn's disease such as the Ashkenazi Jewish population.

The methods of the invention are practiced by determining the presence or absence of IgA anti-I2 antibodies in a subject having Crohn's disease. As used herein, the term "IgA anti-I2 antibodies" means IgA antibodies that selectively bind to an I2 antigen, as well as fragments of antibodies that retain a selective binding activity for an I2 antigen of at least about $1 \times 10^5$ $M^{-1}$. Antibodies that selectively bind an I2 antigen bind with substantially higher affinity to that antigen than to an unrelated antigen. One skilled in the art understands that other isotypes of anti-I2 antibodies, such as IgG, IgM, IgE, and IgD anti-I2 antibodies, also can be useful in the methods of the invention An I2 antigen is a polypeptide having substantially the same amino, acid sequence as the microbial I2 polypeptide (SEQ ID NO: 2) shown in FIG. 1. The naturally occurring microbial I2 antigen SEQ ID NO: 2 is a polypeptide of 100 amino acids sharing some similarity to bacterial transcriptional regulators, with the greatest similarity in the amino-terminal 30 amino acids. The naturally occurring I2 SEQ ID NO:2 shares weak homology with the predicted protein 4 from *C. pasteurianum*; Rv3557c from *Mycobacterium tuberculosis*; and a transcriptional regulator from *Aquifex aeolicus*.

The I2 antigen (SEQ ID NO:2) was originally identified by overexpression of the encoding nucleic acid sequence in colonic microbes harbored in inflamed lesions in Crohn's disease patients (Sutton et al., *Gastroenterology* 119:23-31 (2000)). ELISA analysis showed frequent IgA serum seroreactivity to a recombinant I2 antigen in patients with Crohn's disease but infrequent seroreactivity in patients with ulcerative colitis, other inflammatory enteric disease, or normal individuals (Sutton et al., supra, 2000). The I2 antigen is also known to induce a proliferative and IL-10 response by CD4 (+) T cells in unimmunized mice (Dalwadi et. al., *Immunity* 15:149-158 (2001)). The I2 response is dependent on MHC class II-mediated recognition and does not require antigen processing. Furthermore, activation is observed for the TCR-Vbeta5 subpopulation of cells, indicating that the I2 antigen is a T cell superantigen (Dalwadi et al., supra, 2001). A microbial homologue of I2, PA2885, has been identified in the *Pseudomonas aeruginosa* genome (Wei et al., *Infect. Immun.* 70:6567-6575 (2002)). Furthermore, genomic cloning identified a locus containing the full-length I2 gene (pfiT) in *P. aeruginosa* (Wei et al., supra, 2002).

An I2 antigen can be the naturally occurring I2 antigen SEQ ID NO: 2 or a related polypeptide having substantial amino acid sequence similarity to this sequence. Such related polypeptides generally exhibit greater sequence similarity to the I2 antigen SEQ ID NO: 2 than to related sequences such as the predicted protein 4 from *C. pasteurianum* and include isotype variants or homologs of the amino acid sequence shown in FIG. 1. As used herein, the term I2 antigen generally describes polypeptides having an amino acid sequence with greater than about 60% identity, greater than about 70% identity, greater than about 80% identity, and can be a polypeptide having greater than about 90%, 95%, 97%, or 99% amino acid sequence identity with SEQ ID NO: 2, said amino acid identity determined with CLUSTALW using the BLOSUM 62 matrix with default parameters. The *C. pasteurianum* protein 4 has about 21% amino acid identity with the I2 antigen SEQ ID NO: 2 and, therefore, is not an I2 antigen as defined herein.

As disclosed above, the invention provides a method of diagnosing or predicting susceptibility to a clinical subtype of Crohn's disease in a subject having Crohn's disease by determining the presence or absence of IgA anti-I2 antibodies in the subject, where the presence of the IgA anti-I2 antibodies indicates that the subject has a clinical subtype of Crohn's disease. In one embodiment, the clinical subtype of Crohn's disease is a fibrostenotic subtype of Crohn's disease. In another embodiment, the clinical subtype of Crohn's disease is characterized by the need for small bowel surgery. In a further embodiment, the clinical subtype of Crohn's disease is characterized by the absence of features of ulcerative colitis.

Crohn's disease represents a number of heterogeneous disease subtypes that affect the gastrointestinal tract and may produce similar symptoms. As used herein in reference to Crohn's disease, the term "clinical subtype" means a classification of Crohn's disease defined by a set of clinical criteria that distinguish one classification of Crohn's disease from another. As non-limiting examples, subjects with Crohn's disease can be classified as having fibrostenotic disease, internal-perforating disease, perianal fistulizing disease, ulcerative colitis (UC)-like disease, the need for small bowel surgery or the absence of features of ulcerative colitis. Criteria relating to these subtypes have been described, for example, in Gasche et al., *Inflammatory Bowel Diseases* 6:8-15 (2000); Vasiliauskas et al., *Gut* 47:487-496 (2000); Vasiliauskas et al., *Gastroenterology* 110:1810-1819 (1996); and Greenstein et al., *Gut* 29:588-592 (1988).

The "fibrostenotic subtype" of Crohn's disease is a classification of Crohn's disease characterized by one or more accepted characteristics of fibrostenosing disease. Such characteristics of fibrostenosing disease include, for example, documented persistent intestinal obstruction or an intestinal resection for an intestinal obstruction. The fibrostenotic subtype of Crohn's disease can be accompanied by other symptoms such as perforations, abscesses or fistulae, and further can be characterized by persistent symptoms of intestinal blockage such as nausea, vomiting, abdominal distention and inability to eat solid food. Intestinal X-rays of patients with the fibrostenotic subtype of Crohn's disease can show, for example, distention of the bowel before the point of blockage.

The requirement for small bowel surgery in a subject with the fibrostenotic subtype of Crohn's disease can indicate a more aggressive form of this subtype. As shown in Example I, patients expressing IgA anti-I2 antibodies were significantly more likely to have the fibrostenotic subtype of Crohn's disease and significantly more likely to require small bowel surgery than those not expressing IgA anti-I2 antibodies. In addition, the amplitude or level of IgA anti-I2 antibodies in a subject can be correlated with the likelihood of having a particular clinical subtype of Crohn's disease. As shown in Example I, quartile analyses revealed that higher levels of IgA anti-I2 antibodies were more strongly associated with the fibrostenotic subtype of Crohn's disease and small bowel involvement and were negatively associated with ulcerative colitis-like Crohn's disease than were lower levels. Furthermore, the greater the number of fibrostenotic markers that a subject possesses, the greater chance that the subject will have an aggressive form of the fibrostenotic subtype of Crohn's disease requiring small bowel surgery (see Example I). For example, a subject with two or more markers can have a more severe form of the fibrostenotic subtype than a patient with one marker.

Additional subtypes of Crohn's disease also are known in the art and can be identified using defined clinical criteria. For example, internal perforating disease is a clinical subtype of Crohn's disease defined by current or previous evidence of entero-enteric or entero-vesicular fistulae, intra-abdominal abscesses, or small bowel perforation. Perianal perforating disease is a clinical subtype of Crohn's disease defined by current or previous evidence of either perianal fistulae or abscesses or rectovaginal fistula. The UC-like clinical subtype of Crohn's disease can be defined by current or previous evidence of left-sided colonic involvement, symptoms of bleeding or urgency, and crypt abscesses on colonic biopsies. Disease location can be classified based on one or more endoscopic, radiologic or pathologic studies.

One skilled in the art understands that overlap can exist between clinical subtypes of Crohn's disease and that a subject having Crohn's disease can have more than one clinical subtype of Crohn's disease. For example, a subject having Crohn's disease can have the fibrostenotic subtype of Crohn's disease and can also meet clinical criteria for a clinical subtype characterized by the need for small bowel surgery or the internal perforating disease subtype. Similarly, the markers described herein can be associated with more than one clinical subtype. For example, IgA anti-OmpC antibodies can be associated with the fibrostenotic subtype, need for small bowel surgery, and internal perforating disease subtypes, and can be independently associated with the internal perforating disease subtype. Also, for example, ASCA can be independently associated with the fibrostenotic subtype, a clinical subtype characterized by the need for small bowel surgery, and the internal perforating disease subtype.

The invention further provides a method of diagnosing or predicting susceptibility to a clinical subtype of Crohn's disease in a subject having Crohn's disease by contacting a sample from the subject with an I2 antigen, or immunoreactive fragment thereof, under conditions suitable to form a complex of I2 antigen, or immunoreactive fragment thereof, and antibody against the I2 antigen; contacting the complex with a labeled secondary antibody; and detecting the presence or absence of the complex, where the presence of the complex indicates the presence of the IgA anti-I2 antibodies in the subject, thereby indicating that the subject has a clinical subtype of Crohn's disease.

The invention additionally provides a method of diagnosing or predicting susceptibility to a fibrostenotic subtype of Crohn's disease in a subject having Crohn's disease by contacting a sample from the subject with an I2 antigen, or immunoreactive fragment thereof, under conditions suitable to form a complex of I2 antigen, or immunoreactive fragment thereof, and antibody against the I2 antigen; contacting the complex with a labeled secondary antibody; and detecting the presence or absence of the complex, where the presence of the complex indicates the presence of the IgA anti-I2 antibodies in the subject, thereby indicating that the subject has the fibrostenotic subtype of Crohn's disease.

A sample useful in the methods of the invention can be obtained from any biological fluid having antibodies such as, for example, whole blood, plasma, saliva, or other bodily fluid or tissue, such as serum. It is understood that a sample to be assayed according to the methods of the invention can be a fresh or preserved sample obtained from a subject to be diagnosed.

As used herein, the term "complex" is synonymous with "immune complex" and means an aggregate of two or more molecules that results from specific binding between an antigen, such as a protein or peptide, and an antibody. In a method of the invention, a complex is formed, for example, by specific binding of an antibody and an I2 antigen or immunoreaction fragment thereof.

As used herein, the term "I2 antigen" means a polypeptide which is immunoreactive with IgA anti-I2 antibodies that immunoreact with SEQ ID NO:2. For example, the amino acid sequence SEQ ID NO:2 can be an I2 antigen. An immunoreactive fragment of the I2 antigen also can be used in the methods of the invention. As used herein, the term "immunoreactive fragment" means a portion of a full-length I2 antigen that retains the ability to form a specific complex with IgA anti-I2 antibodies.

An I2 antigen, or immunoreactive fragment thereof, useful in the invention can be produced or synthesized using methods well known in the art. Such methods include recombinant DNA methods and chemical synthesis methods for production of a peptide. Recombinant methods for producing a polypeptide antigen through expression of a nucleic acid sequence encoding the polypeptide in a suitable host cell are well known in the art and are described, for example, in Ausubel et al., supra, 1999.

An I2 antigen, or immunoreactive fragment thereof, useful in the invention also can be produced by chemical synthesis, for example, by the solid phase peptide synthesis method of Merrifield et al., *J. Am. Chem. Soc.* 85:2149 (1964). Standard solution methods well known in the art also can be used to synthesize an I2 antigen, or immunoreactive fragment thereof (see, for example, Bodanszky, *Principles of Peptide Synthesis*, Springer-Verlag, Berlin (1984) and Bodanszky, *Peptide Chemistry*, Springer-Verlag, Berlin (1993)). A newly synthesized polypeptide antigen or immunogenic fragment thereof can be purified, for example, by high performance liquid chromatography (HPLC), and can be characterized using, for example, mass spectrometry or amino acid sequence analysis.

It is understood that limited modifications can be made to an I2 antigen without destroying its ability to bind to IgA anti-I2 antibodies. Similarly, limited modifications can be made to an immunoreactive fragment of an I2 antigen without destroying its immunoreactivity. A modification of an antigen disclosed herein that does not destroy its reactivity with IgA antibodies in the sera of patients having Crohn's disease is within the definition of an I2 antigen. Similarly, a modification of an immunoreactive fragment of an I2 antigen disclosed herein that does not destroy its ability to form a complex with IgA antibodies in the sera of a patient having Crohn's disease is within the definition of an immunoreactive fragment. A modification can be, for example, an addition, deletion, or substitution of amino acid residues; substitution of a compound that mimics amino acid structure or function; or addition of chemical moieties such as amino or acetyl groups. The activity of a modified I2 antigen or a modified immunoreactive fragment of an I2 antigen can be assayed, for example, using one of the assays for immunoreactivity disclosed herein.

A useful modification, for example, is one that confers increased stability. Incorporation of one or more D-amino acids is a modification useful in increasing stability of an I2 antigen or immunoreactive fragment thereof. Similarly, deletion or substitution of lysine can increase stability by protecting against degradation. For example, such a substitution can increase stability of an I2 antigen or an immunoreactive fragment thereof, provided that the substitution does not significantly impair immunoreactive activity.

In the methods of the invention, a complex can be detected with a labeled secondary antibody, for example, that has specificity for a class determining portion of an anti-I2 antibody. Such a secondary antibody can be, without limitation, an anti-IgA secondary antibody, an anti-IgG secondary antibody, or a combination of anti-IgA and anti-IgG secondary antibodies.

As used herein, the term "secondary antibody" means an antibody or combination of antibodies, which binds an antibody that specifically binds an I2 antigen, or an immunoreactive fragment thereof. One skilled in the art understands that, preferably, a secondary antibody does not compete with the I2 antigen for binding to the primary antibody. A secondary antibody can bind any epitope of an anti-I2 antibody. A particularly useful secondary antibody is an anti-IgA or anti-IgG antibody having specificity for the class determining portion of the primary antibody.

It is understood that a useful secondary antibody is specific for the species from which the sample was obtained. For example, if human serum is the sample to be assayed, mouse anti-human IgA or IgG can be a useful secondary antibody. A combination of different antibodies, which can be useful in the methods of the invention, also is encompassed within the meaning of the term secondary antibody, provided that at least one antibody of the combination reacts with an antibody that specifically binds an I2 antigen.

The term class determining portion, when used in reference to a secondary antibody, means the heavy chain constant-region sequence of an antibody that determines the isotype, such as IgA, IgD, IgE, IgG or IgM. Thus, a secondary antibody that has specificity for the class determining portion of an IgA molecule, for example, binds IgA in preference to other antibody isotypes.

A secondary antibody useful in the invention can be obtained commercially or by techniques well known in the art. Such an antibody can be a polyclonal or a monoclonal antibody. For example, IgA reactive polyclonal antibodies can be prepared using IgA or Fc fragments of IgA as an immunogen to stimulate the production of antibodies in the antisera of an animal such as a rabbit, goat, sheep or rodent, as described in Harlow and Lane, *Antibodies: A Laboratory Manual* New York: Cold Spring Harbor Laboratory (1988). Monoclonal secondary antibodies, which are a population of antibody molecules that contain only one species of idiotype capable of binding a particular antigen epitope also can be produced by routine methods (see, for example, Harlow and Lane, supra, 1988) or obtained commercially.

The term "labeled secondary antibody" means a secondary antibody, as defined above, that can be detected or measured by analytical methods. Thus, the term labeled secondary antibody includes an antibody labeled directly or indirectly with a detectable marker that can be detected or measured and used in a convenient assay such as an enzyme-linked immunosorbent assay (ELISA), fluorescent assay, radioimmunoassay, radial immunodiffusion assay or Western blotting assay. A secondary antibody can be labeled, for example, with an enzyme, radioisotope, fluorochrome or chemiluminescent marker. In addition, a secondary antibody can be rendered detectable using a biotin-avidin linkage such that a detectable marker is associated with the secondary antibody. Labeling of the secondary antibody, however, should not impair binding of the secondary antibody to the I2 antigen. If desired, a multiple antibody system can be used as discussed above. In such a system, at least one of the antibodies is capable of binding the primary anti-I2 antibody and at least one of the antibodies can be readily detected or measured by analytical methods.

A secondary antibody can be rendered detectable by labeling with an enzyme such as horseradish peroxidase (HRP), alkaline phosphatase (AP), β-galactosidase or urease, for example. A horseradish-peroxidase detection system can be used, for example, with the chromogenic substrate tetramethylbenzidine (TMB), which yields a soluble product in the presence of hydrogen peroxide that is detectable by measuring absorbance at 450 nm. An alkaline phosphatase detection system can be used with the chromogenic substrate p-nitrophenyl phosphate, for example, which yields a soluble product readily detectable by measuring absorbance at 405 nm. Similarly, a β-galactosidase detection system can be used with the chromogenic substrate o-nitrophenyl-β-D-galactopyranoside (ONPG), which yields a soluble product detectable by measuring absorbance at 410 nm, or a urease detection system can be used with a substrate such as urea-bromocresol purple (Sigma Immunochemicals, St. Louis, Mo.). A secondary antibody can be linked to an enzyme by methods well known in the art (Harlow and Lane, supra, 1988) or can be obtained from a number of commercial sources. For example, goat F(ab')2 anti-human IgA-alkaline phosphatase is a useful detectable secondary antibody that can be purchased from Jackson Immuno-Research (West Grove, Pa.).

A secondary antibody also can be rendered detectable by labeling with a fluorochrome. Such a fluorochrome emits light of ultraviolet or visible wavelength after excitation by light or another energy source. DAPI, fluorescein, Hoechst 33258, R-phycocyanin, B-phycoerythrin, R-phycoerythrin, rhodamine, Texas red or lissamine are, without limitation, fluorochromes that can be linked to a secondary antibody and used to detect the presence or absence of a complex in a method of the invention. Methods of conjugating and using these and other suitable fluorochromes are described, for example, in Van Vunakis and Langone, *Methods in Enzymology*, Volume 74, Part C (1991). A secondary antibody linked to a fluorochrome also can be obtained from commercial sources. For example, goat F(ab')$_2$ anti-human IgA-FITC is available from Tago Immunologicals (Burlingame, Calif.).

A secondary antibody also can be labeled with a chemiluminescent marker. Such a chemiluminescent secondary antibody is convenient for sensitive, non-radioactive detection of a complex containing an I2 antigen and can be obtained commercially from various sources such as Amersham Lifesciences, Inc. (Arlington Heights, Ill.).

A secondary antibody further can be rendered detectable by labeling with a radioisotope. For example, an iodine-125 labeled secondary antibody is a useful detectable secondary antibody (see, for example, Harlow and Lane, supra, 1988).

A signal from a detectable secondary antibody can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis can be made using a spectrophotometer such as an EMAX Microplate Reader (Molecular Devices; Menlo Park, Calif.) in accordance with the manufacturer's instructions. If desired, the assays of the invention can be automated or performed robotically, and the signal from multiple samples can be detected simultaneously.

The assays of the present invention can be forward, reverse or simultaneous as described in U.S. Pat. No. 4,376,110, issued Mar. 8, 1983, to David et al. In the forward assay, each reagent is sequentially contacted with an I2 antigen of the invention. If desired, separation of bound from unbound reagent can be performed before the addition of the next reagent. In a reverse assay, all reagents are pre-mixed prior to contacting with I2 antigen. A modified reverse assay is described in U.S. Pat. No. 4,778,751 issued Oct. 18, 1988, to El Shami et al. In a simultaneous assay, all reagents are separately but contemporaneously contacted with an I2 antigen of the invention. A reagent is any component useful in performing the assays of the present invention, for example, the sample, I2 antigen, detectable secondary antibody, washing buffer or other solutions.

Separation steps for the various assay formats described herein, including the removal of unbound secondary antibody from the complex, can be performed by methods known in the art (Harlow and Lane, supra, 1988). For example, washing with a suitable buffer can be followed by filtration, aspiration or magnetic separation. If the I2 antigen or an immunoreactive fragment thereof is immobilized on a particulate support, such as on microparticles, the particulate material can be centrifuged, if desired, followed by removal of wash liquid. If the I2 antigen or an immunoreactive fragment thereof is immobilized on a membrane, filter or well, a vacuum or liquid absorbing apparatus can be applied to the opposite side of the membrane, filter or well to draw the wash liquid away from the complex.

Antibody based methods can also be useful for determining the presence or absence of IgA anti-I2 antibodies, anti-*Saccharomyces cerevisiae* antibodies or other antibodies such as IgA anti-OmpC antibodies, and perinuclear anti-neutrophil cytoplasmic antibodies. Such methods rely on anti-idiotypic antibodies specific to the anti-I2 or other antibody of interest. An anti-idiotypic antibody contains an internal image of the antigen used to create the antibody of interest. Therefore, an anti-idiotypic antibody can bind to an anti-I2 antibody or other marker antibody of interest. Methods of making, selecting and using anti-idiotype antibodies are well known in the art. See, for example, Eichmann, et al., *CRC Critical Reviews in Immunology* 7:193-227 (1987).

A method of the invention for diagnosing or predicting susceptibility to a clinical subtype of Crohn's disease in a subject having Crohn's disease by determining the presence or absence of IgA anti-I2 antibodies in the subject can optionally include the additional step of determining the presence or absence in the subject of a NOD2 variant, anti-*Saccharomyces cerevisiae* antibodies, IgA anti-OmpC antibodies, or perinuclear anti-neutrophil cytoplasmic antibodies (pANCA).

As used herein, the term "marker" means a serological, genetic or other biochemical factor, the presence of which correlates with a clinical subtype of Crohn's disease. Markers for clinical subtypes of Crohn's disease include, without limitation, IgA anti-I2 antibodies, NOD2 variants, anti-*Saccharomyces cerevisiae* antibodies, IgA anti-OmpC antibodies, and perinuclear anti-neutrophil cytoplasmic antibodies. As used herein, the term "fibrostenotic marker" means a serological, genetic or other biochemical factor, the presence of which correlates with the fibrostenotic subtype of Crohn's disease. Non-limiting examples of fibrostenotic markers useful in the invention include IgA anti-I2 antibodies; NOD2 variants such as R702W, G908R and 1007fs; anti-*Saccharomyces cerevisiae* antibodies; anti-OmpC antibodies; antibodies to other bacterial responsive antigens, and markers associated with other types of fibrostenotic disease such as fibrostenosis of the liver. As shown in Example I, the greater the number of fibrostenotic markers that a subject possesses, the greater the chance that the subject will have an aggressive form of the fibrostenotic subtype of Crohn's disease requiring small bowel surgery.

A NOD2 variant is a fibrostenotic marker useful in the methods of the invention. As used herein, the term "NOD2 variant" means a nucleotide sequence of a NOD2 gene containing one or more changes as compared to the wild-type NOD2 gene or an amino acid sequence of a NOD2 polypeptide containing one or more changes as compared to the wild-type NOD2 polypeptide sequence. NOD2, also known as CARD15, has been localized to the IBD1 locus on chromosome 16 and identified by positional-cloning (Hugot et al., Nature 411:599-603 (2001)) as well as a positional candidate gene strategy (Ogura et al., Nature 411:603-606 (2001), Hampe et al., Lancet 357:1925-1928 (2001)). The IBD1 locus has a high multipoint linkage score (MLS) for inflammatory bowel disease (MLS=5.7 at marker D16S411 in 16q12). See Cho et al., Inflamm. Bowel Dis. 3:186-190 (1997), Akolkar et al., Am. J. Gastroenterol. 0.96:1127-1132 (2001), Ohmen et al., Hum. Mol. Genet. 5:1679-1683 (1996), Parkes et al., Lancet 348:1588 (1996), Cavanaugh et al., Ann. Hum. Gent. (1998), Brant et al., Gastroenterology 115:1056-1061 (1998), Curran et al., Gastroenterology 115:1066-1071. (1998), Hampe et al., Am. J. Hum. Genet. 64:808-816 (1999), and Annese et al., Eur. J. Hum. Genet. 7:567-573 (1999).

The sequence of the human NOD2 gene can be found in GenBank as accession number NM_022162. In addition, the complete sequence of human chromosome 16 clone RP11-327F22, which includes NOD2, can be found in GenBank as accession number AC007728. Furthermore, the sequence of NOD2 from other species can be found in the GenBank database. A schematic of the NOD2 locus is shown in FIG. 2A.

The NOD2 protein contains amino-terminal caspase recruitment domains (CARDs), which can activate NF-kappa B (NF-κB), and several carboxy-terminal leucine-rich repeat domains (Ogura et al, J. Biol. Chem. 276:4812-4818 (2001)). NOD2 has structural homology with the apoptosis regulator Apaf-1/CED-4 and a class of plant disease resistant gene products (Ogura et al., supra, 2001). Similar to plant disease resistant gene products, NOD2 has an amino-terminal effector domain, a nucleotide-binding domain and leucine rich repeats (LRRs). Wild-type NOD2 activates nuclear factor NF-kappa B, making it responsive to bacterial lipopolysaccharides (LPS; Ogura et al., supra, 2001; Inohara et al., J. Biol. Chem. 276:2551-2554 (2001). NOD2 can function as an intercellular receptor for LPS, with the leucine rich repeats required for responsiveness. Three single nucleotide polymorphisms in the coding region of NOD2 have been previously described. These three SNPs, designated R702W, G908R and 1007fs, are located in the carboxy-terminal region of the NOD2 gene (Hugot et al., supra, 2001).

In one embodiment, a NOD2 variant is located in a coding region of the NOD2 locus, for example, within a region encoding several leucine-rich repeats in the carboxy-terminal portion of the NOD2 polypeptide. Such NOD2 variants located in the leucine-rich repeat region of NOD2 include, without limitation, R702W and G908R. A NOD2 variant useful in the invention also can encode a NOD2 polypeptide with reduced ability to activate NF-kappa B as compared to NF-kappa B activation by a wild-type NOD2 polypeptide. As an example, the NOD2 variant 1007fs results in a truncated NOD2 polypeptide which has reduced ability to induce NF-kappa B in response to LPS stimulation (Ogura et al., Nature 411:603-606 (2001)).

A NOD2 variant useful in the invention can be, for example, R702W, G908R, or 1007fs. R702W, G908R, and 1007fs are located within the coding region of NOD2 as shown in FIG. 2A. In one embodiment, a method of the invention is practiced with the R702W NOD2 variant. As used herein, the term "R702W" means a single nucleotide polymorphism within exon 4 in the NOD2 gene, which occurs within a triplet encoding amino acid 702 of the NOD2 protein. The wild-type NOD2 allele contains a cytosine (c) residue at position 138,991 of the AC007728 sequence, which occurs within a triplet encoding an arginine at amino acid 702. The R702W NOD2 variant contains a thymine (t) residue at position 138,991 of the AC007728 sequence, resulting in an arginine (R) to tryptophan (W) substitution at amino acid 702 of the NOD2 protein. Accordingly, this NOD2 variant is denoted "R702W" or "702W" and can also be denoted "R675W" based on the earlier numbering system of Hugot et al., supra, 2001. In addition, the R702W variant is also known as the SNP 8 allele or a "2" allele at SNP 8. The NCBI SNP ID number for R702W or SNP 8 is rs2066844. As disclosed herein and described further below, the presence of the R702W NOD2 variant and other NOD2 variants can be conveniently detected, for example, by allelic discrimination assays or sequence analysis. Primers and probes specific for the R702W NOD2 variant can be found in Tables 1 and 2 in Example IV and in FIG. 2B.

A method of the invention also can be practiced with the G908R NOD2 variant. As used herein, the term "G908R" means a single nucleotide polymorphism within exon 8 in the NOD2 gene, which occurs within a triplet encoding amino acid 908 of the NOD2 protein (see FIG. 2C). Amino acid 908 is located within the leucine rich repeat region of the NOD2 gene. The wild-type NOD2 allele contains a guanine (g) residue at position 128,377 of the AC007728 sequence, which occurs within a triplet encoding glycine at amino acid 908. The G908R NOD2 variant contains a cytosine (c) residue at position 128,377 of the AC007728 sequence, resulting in a glycine (G) to arginine (R) substitution at amino acid 908 of the NOD2 protein. Accordingly, this NOD2 variant is denoted "G908R" or "908R" and can also be denoted "G881R" based on the earlier numbering system of Hugot et al., supra, 2001. In addition, the G908R variant is also known as the SNP 12 allele or a "2" allele at SNP12. The NCBI SNP ID number for G908R SNP 12 is rs2066845. Primers and probes specific for the G908R NOD2 variant can be found in Tables 1 and 2 in Example IV and in FIG. 2C.

A method of the invention also can be practiced with the 1007fs NOD2 variant. This variant is an insertion of a single nucleotide that results in a frame shift in the tenth leucine-rich repeat of the NOD2 protein and is followed by a premature stop codon. The resulting truncation of the NOD2 protein appears to prevent activation of NF-kappaB in response to bacterial lipopolysaccharides (Ogura et al., supra, 2001). As used herein, the term "1007fs" means a single nucleotide polymorphism within exon 11 in the NOD2 gene, which occurs in a triplet encoding amino acid 1007 of the NOD2 protein. The 1007fs variant contains a cytosine which has been added at position 121,139 of the AC007728 sequence, resulting in a frame shift mutation at amino acid 1007. Accordingly, this NOD2 variant is denoted "1007fs" and can also be denoted "3020insC," or "980fs" based on the earlier numbering system of Hugot et al., supra, 2001. In addition, the 1007fs NOD2 variant is also known as the SNP 13 allele or a "2" allele at SNP 13. The NCBI SNP ID number for 1007fs or SNP 13 is rs2066847. Primers and probes specific for the 1007fs NOD2 variant can be found in Tables 1 and 2 in Example IV and in FIG. 2D.

One skilled in the art recognizes that a particular NOD2 variant or other polymorphic allele can be conveniently defined, for example, in comparison to a Centre d'Etude du Polymorphisme Humain (CEPH) reference individual such as the individual designated 1347-02 (Dib et al., Nature 380: 152-154 (1996)), using commercially available reference DNA obtained, for example, from PE Biosystems (Foster City, Calif.). In addition, specific information on SNPs can be obtained from the dbSNP of the National Center for Biotechnology Information (NCBI).

A NOD2 Variant also can be located in a non-coding region of the NOD2 locus. Non-coding regions include, for example, intron sequences as well as 5' and 3' untranslated sequences. A non-limiting example of a NOD2 variant located in a non-coding region of the NOD2 gene is the JW1 variant, which is described in Sugimura et al., Am. J. Hum. Genet. 72:509-518 (2003). It is understood that the methods of the invention can be practiced with JW1 or other NOD2 variants located in a non-coding region of the NOD2 locus, such as an intron or promoter region of the NOD2 locus. It is further understood that the methods of the invention can involve determining the presence of one, two, three, four or more NOD2 variants, including, but not limited to, the R702W, G908R, 1007fs, JW1 and other coding and non-coding region variants.

A variety of means can be useful for determining the presence or absence of a NOD2 variant in a method of the invention. Since a NOD2 variant can be a nucleotide sequence of a NOD2 gene containing one or more changes as compared to the wild-type NOD2 gene or an amino acid sequence of an NOD2 polypeptide containing one or more changes as compared to the wild-type NOD2 polypeptide sequence, genetic, serological and other biochemical methods can be useful. As an example, enzymatic amplification of nucleic acid from a subject can be conveniently used to obtain nucleic acid for subsequent genetic analysis. The presence or absence of a NOD2 variant also can be determined directly from the individual's nucleic acid without enzymatic amplification. Analysis of nucleic acid from a subject, whether amplified or not, can be performed using any of various techniques, including, without limitation, polymerase chain reaction based analysis, sequence analysis and electrophoretic analysis. Techniques can be used alone or in combination.

The presence or absence of a NOD2 variant or another genetic marker can involve amplification of an individual's nucleic acid by the polymerase chain reaction. The nucleic acid to be amplified can be a single- or double-stranded DNA or RNA molecule, including, for example, genomic DNA, cDNA and mRNA. Use of the polymerase chain reaction for amplification of nucleic acids is well known in the art (see, for example, Mullis et al. (Eds.), The Polymerase Chain Reaction, Birkhäuser, Boston, (1994)). Polymerase chain reaction amplification for determining the presence of a NOD2 variant or other genetic marker can be performed, if desired, using one or more fluorescently labeled primers, or using one or more labeled or unlabeled primers that contain a DNA minor grove binder, as in the Taqman® assay described below.

Any of a variety of different primers can be used to amplify an individual's nucleic acid by the polymerase chain reaction in order to determine the presence or absence of a NOD2 variant or other genetic marker in a method of the invention. For example, the PCR primers listed in Table 1 (SEQ ID NOS: 11-16) can be used to amplify specific regions of the NOD2 locus. As non-limiting examples, the region surrounding R702W can be amplified using SEQ ID NO: 11 and 12; G908R can be amplified using SEQ ID NOS: 13 and 14, and the region surrounding 1007fs can be amplified using SEQ ID NOS: 15 and 16. As understood by one skilled in the art, additional primers for PCR analysis can be designed based on the sequence flanking the NOD2 or other region of interest.

Such primers generally contain about 12 to 30 nucleotides of a sequence upstream or downstream of the region of interest and are generally designed to have sufficient guanine and cytosine content to attain a high melting temperature which allows for a stable annealing step in the amplification reaction. Several computer programs, such as Primer Select, are available to aid in the design of PCR primers.

A Taqman® allelic discrimination assay available from Applied Biosystems can be useful for determining the presence or absence of a NOD2 variant or other genetic marker in a method of the invention. In a Taqman® allelic discrimination assay, a specific, fluorescent, dye-labeled probe for each allele is constructed. Each probe contains a different fluorescent reporter dye such as FAM or VICTM to differentiate the amplification of each allele. In addition, each probe has a quencher dye at one end which reduces fluorescence by fluorescence resonance energy transfer (FRET). During PCR, each probe anneals specifically to complementary sequences in the nucleic acid from the individual. The 5' nuclease activity of Taq polymerase is used to cleave only probe that specifically hybridizes to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. It is understood that improved specificity in allelic discrimination assays can be achieved by conjugating, a DNA minor grove binder (MGB) group to a DNA probe as described, for example, in Kutyavin et al., Nucleic Acids Research 28:655-661 (2000). Minor grove binders include, but are not limited to, compounds such as dihydrocyclopyrroloindole tripeptide (DPI3).

Sequence analysis also can be useful for determining the presence or absence of a NOD2 variant or other genetic marker in a method of the invention. A NOD2 variant can be detected by sequence analysis using primers disclosed herein, for example, the PCR primers listed in Table 1 (SEQ ID NOS: 11-16). As understood by one skilled in the art, additional primers for sequence analysis can be designed based on the sequence flanking the NOD2 region of interest. As a non-limiting example, a sequence primer can contain about 15 to 30 nucleotides of a sequence about 40 to 400 base pairs upstream or downstream of the region of interest. Such sequencing primers are generally designed to have sufficient guanine and cytosine content to attain a high melting temperature which allows for a stable annealing step in the sequencing reaction.

Sequence analysis refers to any manual or automated process by which the order of nucleotides in the nucleic acid is determined. As an example, sequence analysis can be used to determine the nucleotide sequence of a sample of DNA. The term sequence analysis encompasses, without limitation, chemical and enzymatic methods such as dideoxy enzymatic methods including, for example, Maxam-Gilbert and Sanger sequencing as well as variations thereof. The term sequence analysis further encompasses, but is not limited to, capillary array DNA sequencing, which relies on capillary electrophoresis and laser-induced fluorescence detection and can be performed using instruments such as the MegaBACE 1000 or ABI 3700. As additional non-limiting examples, the term sequence analysis encompasses thermal cycle sequencing (Sears et al., Biotechniques 13:626-633 (1992)); solid-phase sequencing (Zimmerman et al., Methods Mol. Cell Biol. 3:39-42 (1992); and sequencing with mass spectrometry such as matrix-assisted laser desorption/ionization time-of-flight mass spectrometry MALDI-TOF MS (Fu et al., *Nature Biotech.* 16: 381-384 (1998)). The term sequence analysis also includes, yet is not limited to, sequencing by hybridization (SBH), which relies on an array of all possible short oligonucleotides to identify a segment of sequences present in an unknown DNA (Chee et al., *Science* 274:610-614 (1996); Drmanac et al., *Science* 260:1649-1652 (1993); and Drmanac et al., *Nature Biotech.* 16:54-58 (1998)). One skilled in the art understands that these and additional variations are encompassed by the term sequence analysis as defined herein. See, in general, Ausubel et al., supra, Chapter 7 and supplement 47.

Genetic methods for determining the presence or absence of a NOD2 variant or other genetic marker utilize a subject's biological matter from which nucleic acid can be prepared. As non-limiting examples, a subject's biological matter can be whole blood, plasma, saliva, cheek swab, or other bodily fluid or tissue that contains nucleic acid. In one embodiment, detecting the presence or absence of a NOD2 variant or other genetic marker is practiced with whole blood, which can be obtained readily by non-invasive means and used to prepare genomic DNA, for example, for enzymatic amplification or automated sequencing. In another embodiment, detecting the presence or absence of a NOD2 variant or other genetic marker is practiced with tissue obtained from an individual such as tissue obtained during surgery or biopsy procedures.

Electrophoretic analysis also can be useful in the methods of the invention. Elecrophoretic analysis, as used herein in reference to one or more nucleic acids such as amplified fragments, means a process whereby charged molecules are moved through a stationary medium under the influence of an electric field. Electrophoretic migration separates nucleic acids primarily on the basis of their charge, which is in proportion to their size, with smaller molecules migrating more quickly. The term electrophoretic analysis includes, without limitation, analysis using slab gel electrophoresis, such as agarose or polyacrylamide gel electrophoresis, or capillary electrophoresis. Capillary electrophoretic analysis generally occurs inside a small-diameter (50-100 m) quartz capillary in the presence of high (kilovolt-level) separating voltages with separation times of a few minutes. Using capillary electrophoretic analysis, nucleic acids are conveniently detected by UV absorption or fluorescent labeling, and single-base resolution can be obtained on fragments up to several hundred base pairs. Such methods of electrophoretic analysis, and variations thereof, are well known in the art, as described, for example, in Ausubel et al., *Current Protocols in Molecular Biology* Chapter 2 (Supplement 45) John Wiley & Sons, Inca New York (1999).

Restriction fragment length polymorphism (RFLP) analysis also can be useful for determining the presence or absence of a NOD2 variant or other genetic marker in a method of the invention (Jarcho et al. in Dracopoli et al., *Current Protocols in Human Genetics* pages 2.7.1-2.7.5, John Wiley & Sons, New York; Innis et al., (Ed.), *PCR Protocols*, San Diego Academic Press, Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele-specific oligonucleotide hybridization also can be used to detect the presence or absence of a NOD2 variant or other genetic marker. Allele-specific oligonucleotide hybridization is based on the use of a labeled oligonucleotide probe having a sequence perfectly complementary, for example, to the sequence encompassing a NOD2 variant. Under appropriate conditions, the allele-specific probe hybridizes to a nucleic acid containing the NOD2 variant but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a NOD2 variant by using an allele-specific oligonucleotide primer that is perfectly complementary to the nucleotide sequence of the NOD2 variant but which has one or more mismatches as compared to other alleles (Mullis et al., supra, 1994). One skilled in the art understands that the one or more nucleotide mismatches that distinguish between the NOD2 variant and one or more other alleles are often located in the center of an allele-specific oligonucleotide primer to be used in allele-specific oligonucleotide hybridization. In contrast, an allele-specific oligonucleotide primer to be used in PCR amplification generally contains the one or more nucleotide mismatches that distinguish between the subtype-associated and other alleles at the 3' end of the primer.

A heteroduplex mobility assay (HMA) is another well known assay that can be used to detect the presence or absence of a NOD2 variant or other genetic marker in a method of the invention. HMA is useful for detecting the presence of a polymorphic sequence since a DNA duplex carrying a mismatch has reduced mobility in a polyacrylamide gel compared to the mobility of a perfectly base-paired duplex (Delwart et al., *Science* 262:1257-1261 (1993); White et al., *Genomics* 12:301-306 (1992)).

The technique of single strand conformational polymorphism (SSCP) also can be used to detect the presence or absence of a NOD2 variant or other genetic marker in a method of the invention (see Hayashi, *Methods Applic.* 1:34-38 (1991)). This technique is used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also can be used to detect a NOD2 variant or other genetic marker in a method of the invention. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence or absence of a NOD2 variant or other genetic marker are known in the art and useful in the methods of the invention. Other well-known approaches for determining the presence or absence of a NOD2 variant include, without limitation, automated sequencing and RNAase mismatch techniques (Winter et al., *Proc. Natl. Acad. Sci.* 82:7575-7579 (1985)). Furthermore, one skilled in the art understands that, where the presence or absence of multiple NOD2 variants is to be determined, individual NOD2 variants can be detected by the same or any combination of molecular methods. See, in general, Birren et al. (Eds.) *Genome Analysis: A Laboratory Manual* Volume 1 (Analyzing DNA) New York, Cold Spring Harbor Laboratory Press (1997). In addition, one skilled in the art understands that multiple NOD2 variants or other genetic markers can be detected in individual reactions or in a single reaction (a "multiplex" assay). In view of the above, one skilled in the art realizes that the methods of the invention for diagnosing or predicting susceptibility to a clinical subtype of Crohn's disease, such as the fibrostenotic subtype, can be practiced using one or any combination of the well known assays described above or known in the art.

Antibody based methods also can be useful for determining the presence or absence of a NOD2 variant in a method of the invention. As an example, an antibody that is specifically reactive with a NOD2 variant polypeptide or fragment thereof can be used to detect the presence or absence of that NOD2 variant in an individual. Such an antibody can be, for example, specifically reactive with the truncated version of NOD2 generated by the 1007fs NOD2 variant but not reactive with full-length or wild type NOD2.

Antibodies useful in the methods of the invention include, without limitation, monoclonal and polyclonal antibodies, single chain antibodies, chimeric antibodies, bifunctional or bispecific antibodies, humanized antibodies, human antibodies, and complementary determining region (CDR)-grafted antibodies, including compounds which include CDR or antigen-binding sequences, which differentially bind to a polypeptide or fragment encoded by a NOD2 variant but not to other non-variant sequences. Antibody fragments, including Fab, Fab', F(ab')$_2$, and Fv, also can be useful in the methods of the invention as can plastic antibodies or molecularly imprinted polymers (MIPs; Haupt and Mosbauch, *TIBTech* 16:468-475 (1998)). Screening assays to determine differential binding specificity of an antibody are well known in the art (see Harlow et al. (Eds), *Antibodies: A Laboratory Manual*; Cold Spring Harbor Laboratory; Cold Spring Harbor, N.Y. (1988)).

Antibodies useful in a method of the invention can be produced using any method well known in the art, using a polypeptide, or immunogenic fragment thereof, encoded by a NOD2 variant. Immunogenic polypeptides or fragments can be isolated, for example, from natural sources or recombinant host cells, or can be chemically synthesized. Methods for synthesizing such peptides are known in the art as described, for example, in Merrifield, *J. Amer. Chem. Soc.* 85: 2149-2154 (1963), and Krstenansky et al., *FEBS Lett.* 211:10 (1987).

Antibodies that differentially bind to NOD2 variants of the invention can be labeled with a detectable label and used to detect the presence, absence or amount of the encoded polypeptide in vivo, in vitro, or in situ. A moiety, such as a fluorescent molecule, can be linked to an antibody for use in a method of the invention using, for example, carbodiimide conjugation (Bauminger and Wilchek, *Meth. Enzymol.* 70:151-159 (1980)).

In a method of the invention, antibodies that differentially bind to a NOD2 variant can be used in immunoassays to determine the presence or absence of a NOD2 variant in a subject having Crohn's disease. Immunoassays include, without limitation, radioimmunoassays, enzyme-linked immunosorbent assays (ELISAs) and immunoassays with fluorescently labeled antibodies, which are well known in the art. Antibodies can also be used to detect the presence or absence of a NOD2 variant or other fibrostenotic marker in a cell or tissue using immunohistochemistry or other in situ assays. Furthermore; cells containing a polypeptide of interest either on the surface of the cell or internally can be detected by an antibody using assays such as fluorescence activated cell sorting (FACS). One skilled in the art understands that these and other routine assays can be useful for determining the presence or absence of a NOD2 variant according to a method of the invention.

Antibodies can be used to detect the presence or absence of a polypeptide of interest, such as IgA anti-I2 antibodies, an NOD2 variant, anti-*Saccharomyces cerevisiae* antibodies, IgA anti-OmpC antibodies, and perinuclear anti-neutrophil cytoplasmic antibodies, for example, directly from a blood sample. One skilled in the art understands that when the presence or absence of multiple markers is determined, the same or a different sample can be used.

As disclosed above, the invention provides a method of diagnosing or predicting susceptibility to a clinical subtype of Crohn's disease in a subject having Crohn's disease by determining the presence or absence of IgA anti-I2 antibodies in the subject and optionally determining the presence or absence in the subject of anti-*Saccharomyces cerevisiae* antibodies (ASCA).

Anti-*Saccharomyces cerevisiae* antibodies (ASCA) are a fibrostenotic marker useful in the invention. As disclosed herein, the presence of ASCA can be used to diagnose or predict susceptibility to a fibrostenotic subtype of Crohn's disease in a subject having Crohn's disease (see Example I). The presence of ASCA can be determined by well known methods such as by reactivity with purified yeast cell wall phosphopeptidomannan (PPM), which can be prepared, for example, from ATCC strain #38926. Methods for determining the presence of ASCA are exemplified herein in Example III. As used herein, "ASCA" means antibody reactivity against *S. cerevisiae* that is greater than the reactivity observed with control (normal subject) sera analyzed under the same conditions.

Anti-*Saccharomyces cerevisiae* antibodies (ASCA) are characteristically elevated in patients having Crohn's disease although the nature of the *S. cerevisiae* antigen supporting the specific antibody response in Crohn's disease is unknown (Sendid et al., *Clin. Diag. Lab. Immunol.*, 3:219-226 (1996)). These antibodies may represent a response against yeasts present in common food or drink or a response against yeasts that colonize the gastrointestinal tract. Studies with periodate oxidation have shown that the epitopes recognized by ASCA in Crohn's disease patient sera contain polysaccharides. Oligomannosidic epitopes are shared by a variety of organisms including different yeast strains and genera, filamentous fungi, viruses, bacteria and human glycoproteins. Thus, the mannose-induced antibody responses in Crohn's disease may represent a response against a pathogenic yeast organism or may represent a response against a cross-reactive oligomannosidic epitope present, for example, on a human glycoprotein autoantigen. Regardless of the nature of the antigen, elevated levels of serum ASCA are a differential marker for Crohn's disease, with only low levels of ASCA reported in UC patients (Sendid et al., supra, 1996). Using multiple regression analysis, higher ASCA levels in subjects with Crohn's disease were shown to be independently associated with early age of disease onset as well as both fibrostenosing and internal penetrating disease behaviors (Vasiliauskas et al., *Gut* 47:487-497 (2000)).

The presence or absence of ASCA can be determined using an antigen specific for ASCA, which is any antigen or mixture of antigens that is bound specifically by ASCA. Although ASCA antibodies were initially characterized by their ability to bind *S. cerevisiae*, those of skill in the art will understand that an antigen specific for ASCA can be obtained from *S. cerevisiae*, or can be obtained from a variety of other sources so long as the antigen is capable of binding specifically to ASCA antibodies. Accordingly, exemplary sources of an antigen specific for ASCA contemplated for use in the methods of the invention include whole killed yeast cells, such as from the genera *Saccharomyces* and *Candida*, yeast cell wall phosphopeptidomannan (PPM), oligomannosides, neoglycolipids, anti-ASCA idiotypic antibodies, and the like. As described above, different species and strains of yeast, including *Saccharomyces*, can be used as an antigen specific for ASCA in the methods provided herein. For example, *S. cerevisiae* strain Su1, Su2, CBS 1315 or BM 156, or *Candida albicans* strain VW32, can be used as an antigen specific for ASCA in the methods of the invention.

Preparations of yeast cell wall mannans, or phosphopeptidomannans (PPM), are also contemplated herein as antigens specific for ASCA. These water soluble surface antigens can be prepared by appropriate extraction techniques, including autoclaving as described in Example III or can be obtained commercially (see Lindberg et al., *Gut* 33:909-913 (1992)). The acid stable fraction of yeast cell wall PPM also can be useful in the methods of the invention (Sendid et al., supra, 1996). An exemplary PPM for use in diagnosing clinical subtypes of Crohn's disease is derived from *S. cerevisiae* strain ATCC #38926.

Purified oligosaccharide antigens, such as oligomannosides specific for ASCA, also are contemplated for use in determining the presence or absence of ASCA in the methods of the invention. Purified oligomannoside antigens can be converted, if desired, into neoglycolipids as described in Faille et al., *Eur. J. Microbiol. Infect. Dis.* 11:438-446 (1992). One skilled in the art understands that the reactivity of such an oligomannoside antigen with ASCA can be optimized by varying the mannosyl chain length (Frosh et al., *Proc. Natl. Cad. Sci. USA* 82:1194-1198 (1985)); the anomeric configuration (Fukazawa et al., In E. Kurstak (ed.), *Immunology of Fungal Disease*, Marcel Dekker Inc., New York, pp. 37-62 (1989); Nishikawa et al, *Microbiol. Immunol.* 34:825-840 (1990); Poulain et al., *Eur. J. Clin. Microbiol* 23:46-52 (1993); Shibata et al., *Arch. Biochem. Biophys.* 243:338-348 (1985); and Trinel et al., *Infect. Immun.* 60:3845-3851 (1992)); or the position of the linkage (Kikuchi et al., *Planta* 190:525-535 (1993)).

An oligomannoside antigen specific for ASCA can include the mannotetraose Man(1-3)Man(1-2)Man(1-2)Man, and can be purified from PMM as described in Faille et al., supra, 1992. An exemplary neoglycolipid for use in the methods of the invention can be constructed by releasing the oligomannoside from its respective PPM and subsequently coupling the released oligomannoside to 4-hexadecylaniline or the like. These and other antigens specific for ASCA can be used in determining the presence or absence of ASCA in the methods of the invention.

IgA anti-OmpC antibodies are another marker useful for determining a clinical subtype of Crohn's disease in a method of the invention. IgA anti-OmpC antibodies are associated with the fibrostenotic subtype, need for small bowel surgery, and internal perforating disease subtype, and can be independently associated with the internal perforating disease subtype. Provided herein is a method of diagnosing or predicting susceptibility to a clinical subtype of Crohn's disease in a subject having Crohn's disease by determining the presence or absence of IgA anti-OmpC antibodies in the subject, where the presence of IgA anti-OmpC antibodies indicates that the subject has a clinical subtype of Crohn's disease. In one embodiment, the clinical subtype of Crohn's disease is the fibrostenotic subtype. In another embodiment, the clinical subtype of Crohn's disease is the internal perforating disease subtype.

The presence of IgA anti-OmpC antibodies in a subject can indicate that the subject has a fibrostenotic subtype of Crohn's disease. In some cases, the presence of IgA anti-OmpC antibodies can correlate with the presence of ASCA. In some embodiments, the presence of IgA anti-OmpC antibodies and ASCA are determined, while in other embodiments the presence of IgA anti-OmpC antibodies can be used as a surrogate marker for the presence of ASCA.

The outer-membrane protein C (OmpC) is a porin, a class of transmembrane proteins that are found in the outer membranes of bacteria, including gram-negative enteric bacteria such as *E. coli*. The porins in the outer membrane of an *E. coli* cell provide channels for passage of disaccharides, phosphate and similar molecules. Porins can be trimers of identical subunits arranged to form a barrel-shaped structure with a pore at the center (Lodish et al., *Molecular Cell Biology*, Chapter 14 (1995)).

OmpC is one of the major porin proteins found in the outer membranes of bacteria such as *E. coli*. An OmpC antigen can be prepared, for example, from an encoding nucleic acid sequence such as that available as GenBank accession K00541 or as shown in FIG. 3A by methods well known in the art (see, for example, Ausubel et al., *Current Protocols in Molecular Biology* John Wiley & Sons, Inc. New York (1999)). OmpC is similar in structure and function to outer-membrane protein F ("OmpF"). Both assemble as trimers in the outer membrane to form aqueous channels that allow the passive diffusion of small, hydrophilic molecules across the hydrophobic barrier. However, OmpC pores have a diameter of 1.1 nm, while OmpF pores have a diameter of 1.2 nm. This difference results in a slower rate of diffusion through the OmpC pores than through the OmpF pores.

Porin expression can be influenced by environmental conditions, including osmolarity, temperature, growth phase and toxin concentration. For example, in the intestine, where both nutrient and toxic molecule concentrations are relatively high, OmpC, with a smaller pore diameter, is the predominant porin (Pratt et al., *Mol. Micro.*, 20:911-917 (1996)).

The methods of the invention relate to determining the presence or absence of IgA anti-OmpC antibodies in a subject having Crohn's disease. As used herein, the term "IgA anti-OmpC antibodies" means IgA reactivity against an OmpC antigen that is greater than two standard deviations above the mean IgA anti-OmpC reactivity of control (normal) sera analyzed under the same conditions. Detection of IgA anti-OmpC antibodies using an ELISA is described herein in Example V.

Another marker useful in the invention is perinuclear anti-neutrophil cytoplasmic antibodies (pANCA). Previous studies have shown pANCA reactivity in a small portion of patients with Crohn's disease, although these antibodies are elevated more frequently in patients with ulcerative colitis. The reported prevalence in Crohn's disease varies from 0 to 43%, with most studies reporting that 10 to 30% of Crohn's disease patients express pANCA (see, for example, Saxon et al., *J. Allergy Clin. Immunol.* 86:202-210 (1990); Cambridge et al., *Gut* 33:668-674 (1992); Pool et al., *Gut* 3446-50 (1993); and Brokroelofs et al., *Dig. Dis. Sci.* 39:545-549 (1994). In subjects with Crohn's disease, serum pANCA expression characterizes a UC-like clinical phenotype of the disease (Vasiliauskas et al., *Gastroenterology* 110:1810-1819 (1996)).

A method of the invention involves determining the presence or absence of I2 antibodies and optionally determining in a subtype having Crohn's disease, the presence or absence of pANCA in the subject, for example, by reactivity with fixed neutrophil. As used herein, the term "perinuclear antineutrophil cytoplasmic antibody" is synonymous with "pANCA" and refers to an antibody that reacts specifically with a neutrophil to give perinuclear to nuclear staining or cytoplasmic staining with perinuclear highlighting. A method for determining the presence of pANCA in a subject is exemplified herein in Example VI.

In one embodiment, the invention provides a method of diagnosing or predicting susceptibility to a fibrostenotic subtype of Crohn's disease in a subject having Crohn's disease by determining the presence or absence of IgA anti-I2 antibodies in the subject, and further determining the presence or absence in the subject of one or more fibrostenotic markers such as a NOD2 variant, anti-*Saccharomyces cerevisiae* antibodies (ASCA), or anti-OmpC antibodies, where the presence of IgA antibodies or the presence of one of the fibrostenotic markers each independently indicates that the subject has the fibrostenotic subtype of Crohn's disease.

The term "independently" means that the presence of IgA anti-I2 antibodies alone or the presence of one of the fibrostenotic markers alone is sufficient to indicate that the subject has the fibrostenotic subtype of Crohn's disease. As shown in Example I, the presence of IgA antibodies alone indicated that a subject was more likely to have a fibrostenotic subtype of Crohn's disease than those not expressing IgA anti-I2 antibodies (71.4% vs. 43.3%, p<0.001) and significantly more likely to require small bowel surgery (66.7% vs. 37.1%, p<0.001). In addition, as shown in Example I, conditional analysis performed on NOD2 variants and ASCA indicated that IgA anti-I2 antibodies were independently associated with the fibrostenotic subtype (p=0.001 and p=0.005 respectively). Similarly, IgA anti-I2 antibodies were independently associated with small bowel surgery when conditioned on NOD2 variation (p=0.001) or ASCA (p=0.002) (see Example I).

As disclosed herein in Example I, combinations of markers can be diagnostic for a subtype of Crohn's disease. For example, the invention provides a method of diagnosing or predicting susceptibility to a fibrostenotic subtype of Crohn's disease in a subject having Crohn's disease by determining the presence or absence of IgA anti-I2 antibodies in the subject, and further determining the presence or absence of a NOD2 variant in the subject, where the combined presence of IgA anti-I2 antibodies and a NOD2 variant in the subject indicates that the subject has the fibrostenotic subtype of Crohn's disease. In one embodiment, the combined presence of the IgA anti-I2 antibodies and the NOD2 variant in the subject is associated with the fibrostenotic subtype of Crohn's disease with an odds ratio of at least 6.

The strength of an association between one or more markers and a clinical subtype of Crohn's disease can be characterized by a particular odds ratio such as an odds ratio of at least 6. Such an odds ratio can be, for example, at least 6.5, 7.0, 8.0, 9.0 or greater. For example, subjects with three markers such as IgA anti-I2 antibodies, NOD2 variation, and ASCA showed the greatest risk of the fibrostenotic subtype of Crohn's disease (82%, odds Ratio=9.7, p<0.000001) compared with subjects with two markers (74%, odds Ratio=6.0), one marker (48%, odds Ratio=1.9), or none of these markers (33%, odds Ratio=reference group) (see Example I). Methods for determining an odds ratio are well known in the art (see, for example, Schlesselman et al., *Case Control Studies: Design, Conduct and Analysis* Oxford University Press, New York (1982)).

In one embodiment, a marker or markers is associated with a clinical subtype of Crohn's disease with a p value of equal to or less than 0.05. In other embodiments, a marker is associated with a clinical subtype of Crohn's disease with a p value of equal to or less than 0.001. As used herein, the term "p value" is synonymous with "probability value." As is well known in the art, the expected p value for the association between a random marker and a subtype is 1.00. A p value of less than about 0.05 indicates that the marker and a subtype do not appear together by chance but are influenced by positive factors. Generally, the statistical threshold for significance of linkage has been set at a level where false positives would occur once in twenty (p=0.05). In particular embodiments, a marker is associated with a clinical subtype of Crohn's disease, such as the fibrostenotic subtype with a p value of equal to or less than 0.05, 0.04, 0.03, 0.02, 0.01, 0.009, 0.008, 0.007, 0.006, 0.005, 0.004, 0.003, 0.002 or 0.001, or with a p value of less than 0.000001, 0.00001, 0.00095, 0.0009, 0.00085, 0.0008 or 0.0005. It is recognized that, in some cases, p values may need to be corrected, for example, to account for factors such as sample size (number of families), genetic heterogeneity, clinical heterogeneity, or analytical approach (parametric or nonparametric method).

In addition to IgA anti-I2 antibodies and a NOD2 variant, other combinations of markers can be diagnostic of a particular clinical subtype of Crohn's disease. For example, the invention provides a method of diagnosing or predicting susceptibility to a fibrostenotic subtype of Crohn's disease in a subject having Crohn's disease by determining the presence or absence of IgA anti-I2 antibodies in the subject and further determining the presence or absence of ASCA in the subject, where the combined presence of anti-I2 antibodies and ASCA in the subject indicates that the subject has the fibrostenotic subtype of Crohn's disease. In one embodiment, the combined presence of the IgA anti-I2 antibodies and the ASCA in the subject is associated with the fibrostenotic subtype of Crohn's disease with an odds ratio of at least 6. In another embodiment, the combined presence of IgA anti-I2 antibodies, a NOD2 variant, and ASCA in the subject indicates that the subject has the fibrostenotic subtype of Crohn's disease. In a related embodiment, the combined presence of the IgA anti-I2 antibodies, a NOD2 variant, and the ASCA in the subject is associated with the fibrostenotic subtype of Crohn's disease with an odds ratio of at least 9.

The methods of the invention optionally include generating a report indicating the presence or absence in a subject of one or more markers associated with a clinical subtype of Crohn's disease as disclosed herein. The methods of the invention also optionally include generating a report indicating the presence or absence in a subject of a clinical subtype of Crohn's disease, for example, the fibrostenotic subtype, or the risk that a subject has of having or developing a particular subtype of Crohn's disease. A report can be in a variety of forms, including, but not limited to, paper reports, oral reports and electronic reports. For example, a report can be printed on paper, or a report can be an electronic report that is not printed but is transmitted over an electronic medium such as electronic mail or a computer diskette.

The invention also provides a method of predicting a response to therapy in a subject having Crohn's disease by determining the presence or absence in the subject of one or more markers associated with a clinical subtype of Crohn's disease, diagnosing the subject in which the one or more markers are present as having a particular subtype of Crohn's disease, and predicting a response to a therapy based on the diagnosis. The invention also provides a method of optimizing therapy in a subject having Crohn's disease by determining the presence or absence in the subject of one or more markers associated with a clinical subtype of Crohn's disease, diagnosing the subject in which the one or more markers are present as having a particular clinical subtype of Crohn's disease, and treating the subject having a particular clinical subtype of Crohn's disease based on the diagnosis. As an example, treatment for the fibrostenotic subtype of Crohn's disease currently includes surgical removal of the affected, structured part of the bowel.

It is understood that modifications which do not substantially affect the activity of the various embodiments of this invention are also included within the definition of the invention provided herein. Accordingly, the following examples are intended to illustrate but not limit the present invention.

EXAMPLE I

Antibodies Against the Bacterial Sequence I2 are a Marker of the Fibrostenotic Subtype of Crohn's Disease This example shows that antibodies against the Crohn's disease-associated bacterial sequence I2 are an independent marker of the fibrostenotic subtype of Crohn's disease.

Clinical, serologic and genetic data were examined for 258 Crohn's disease patients under an Institutional Review Board (IRB) approved protocol. Briefly, a diagnosis of Crohn's disease in the patients was defined by the presence of a combination of established features from at least two of the following categories: 1) clinical—perforating or fistulizing disease, obstructive symptoms secondary to small bowel stenosis or stricture; 2) endoscopic—deep linear or serpiginous ulcerations, discrete ulcers in normal-appearing mucosa, cobblestoning, or discontinuous or asymmetric inflammation; 3) radiographic—segmental disease (skip lesions), small bowel or colon strictures, stenosis, or fistula, and; 4) histopathologic—submucosal or transmural inflammation, multiple granulomas, marked focal cryptitis or focal chronic inflammatory infiltration within and between biopsies, or skip lesions including rectal sparing in the absence of local therapy. Patients with primary sclerosing cholangitis and autoimmune hepatitis and those with chronically increased transaminase or alkaline phosphatase levels were excluded to avoid confusion with non-inflammatory bowel disease ANCA.

ELISAs were performed for IgA anti-I2 antibodies and anti-*Saccharomyces cerevisiae* antibodies (ASCA) as described in Examples II and III. Genotyping was performed for three Crohn's disease associated variants of the NOD2 gene, R702W, G908R, and 1007fs using the Taqman MGB system as described in Example IV.

Analysis of ELISA and genotyping data indicated that IgA antibodies to I2 were present in 56.5% of the Crohn's disease patients in the study. Patients expressing IgA anti-I2 antibodies were significantly more likely to have a fibrostenotic subtype of Crohn's disease than those not expressing IgA anti-I2 antibodies (71.4% vs. 43.3%, $p<0.001$) and significantly more likely to require small bowel surgery (66.7% vs. 37.1%, $p<0.001$). In addition, IgA anti-I2 antibodies expression was negatively associated with ulcerative colitis-like Crohn's disease (20.6% vs. 41.24%, $p<0.001$). Quartile analyses revealed that higher-levels of IgA anti-I2 antibodies were more strongly associated with the fibrostenotic subtype of Crohn's disease (p for the trend <0.001), small bowel involvement ($p=0.023$), and inversely associated with ulcerative colitis-like Crohn's disease ($p=0.005$).

Conditional analysis performed on NOD2 variants and ASCA indicated that IgA anti-I2 antibodies were independently associated with the fibrostenotic subtype ($p=0.001$ and $p=0.005$, respectively). Similarly, IgA anti-I2 antibodies was independently associated with small bowel surgery when conditioned on NOD2 variation ($p=0.001$) or ASCA ($p=0.002$).

Patients with all three markers, IgA anti-I2 antibodies, NOD2 variation, and ASCA showed the greatest risk of the fibrostenotic subtype of Crohn's disease (82%, Odds Ratio=9.7, $p<0.000001$), compared with patients with two (74%, Odds Ratio=6.0), one (48%, Odds Ratio=1.9), or none of these markers (33%, Odds Ratio=reference group).

EXAMPLE II

ELISA For IgA Anti-I2 Antibodies

This example shows demonstrates that the presence of IgA anti-I2 antibodies in patient sera can be determined using an ELISA microplate, assay.

A. GST-I2 Fusion Protein

The full-length I2 encoding nucleic acid sequence (SEQ ID NO: 1) was cloned into the GST expression vector pGEX. After expression in *E. coli*, the protein was purified on a GST column. A GST control protein was also expressed and purified. The purified protein was shown to be of the expected molecular weight by silver staining, and had anti-GST reactivity upon western analysis. The full-length I2 encoding nucleic acid sequence (SEQ ID NO:1) has also been cloned into a Hex-His, expression vector, expressed in *E. coli*, and the resulting protein purified.

B. ELISA Analysis

Human IgA antibodies that bind the I2 polypeptide (SEQ ID NO: 2) were detected by direct ELISA assays essentially as follows. Plates (Greiner, USA Scientific, Ocala, Fla.) were coated overnight at 4° C. with 100 μl/well GST control polypeptide or GST-I2 fusion polypeptide (5 μg/ml in borate buffered saline, pH 8.5). After three washes in 0.05% Tween 20 in phosphate buffered saline (PBS), the plates were blocked with 150 μl/well of 0.5% bovine serum albumin in PBS, pH 7.4 (BSA-PBS) for 30 minutes at room temperature. The blocking solution was then replaced with 100 μl/well of Crohn's disease or normal control serum, diluted 1:100. The plates were then incubated for 2 hours at room temperature and washed as before. Alkaline phosphatase conjugated goat anti-human IgA (α-chain specific), or IgG (γ chain specific) (Jackson ImmunoResearch, West Grove, Pa.) was added to the plates at a dilution of 1:1000 in BSA-PBS. The plates were incubated for 2 hours at room temperature before washing three times with 0.05% Tween 20/PBS followed by another three washes with Tris buffered normal saline, pH 7.5. Substrate solution (1.5 mg/ml disodium p-nitrophenol phosphate (Aresco; Solon, Ohio) in 2.5 mM $MgCl_2$, 0.01 M Tris, pH 8.6) was added at 100 μl/well, and color allowed to develop for one hour. The plates were then analyzed at 405 nm. Nonspecific binding of sera to the control GST protein (typically <0.1) were subtracted from raw values of I2 binding to obtain I2-specific absorbances.

I2 positive reactivity was defined as reactivity greater than two standard deviations above the mean reactivity obtained with control (normal) sera analyzed at the same time as the test samples.

EXAMPLE III

ELISA for Anti-*Saccharomyces cerevisiae* Antibodies (ASCA)

This example demonstrates that the presence of anti-*Saccharomyces cerevisiae* antibodies in patient sera can be determined using an ELISA microplate assay.

A. Preparation of Yeast Cell Wall Mannan

Yeast cell wall mannan was prepared as follows and as described in Faille et al. *Eur. J. Clin. Microbiol. Infect. Dis.* 11:438-446 (1992) and in Kocourek and Ballou et al., *J. Bacteriol* 100:1175-1181 (1969). A lyophilized pellet of yeast *Saccharomyces uvarum* was obtained from the American Type Culture Collection (#38926). Yeast were reconstituted in 10 ml 2×YT medium, prepared according to Sambrook et al., *Molecular Cloning* Cold Spring Harbor Laboratory Press (1989). *S. uvarum* were grown for two to three days at 30° C. The terminal *S. uvarum* culture was inoculated on a 2×YT agar plate and subsequently grown for two to three days at 30° C. A single colony was used to inoculate 500 ml 2×YT media, and grown for two to three days at 30° C. Fermentation media (pH 4.5) was prepared by adding 20 gm glucose, 2 gm bacto-yeast extract, 0.25 gm $MgSO_4$ and 2.0 ml 28% $H_3PO_4$ per liter distilled water. The 500 ml culture was used to inoculate 50 liters of fermentation media, and the culture fermented for three to four days at 37° C.

*S. uvarum* mannan extract was prepared by adding 50 ml 0.02 M citrate buffer (5.88 gm/l sodium citrate; pH 7.0+/−0.1) to each 100 grams of cell paste. The cell/citrate mixture was autoclaved at 125° C. for ninety minutes and allowed to cool. After centrifuging at 5000 rpm for 10 minutes, the supernatant was removed and retained. The cells were then washed with 75 ml 0.02 M citrate buffer and the cell/citrate mixture again autoclaved at 125° C. for ninety minutes. The cell/citrate mixture was centrifuged at 5000 rpm for 10 minutes, and the supernatant retained.

In order to precipitate copper/mannan complexes, an equal volume of Fehling's Solution was added to the combined supernatants while stirring. The complete Fehling's solution was prepared by mixing Fehling's Solution A with Fehling's Solution B in a 1:1 ratio just prior to use. The copper complexes were allowed to settle, and the liquid decanted gently from the precipitate. The copper/mannan precipitate complexes were then dissolved in 6-8 ml 3N HCl per 100 grams yeast paste.

The resulting solution was poured with vigorous stirring into 100 ml of 8:1 methanol:acetic acid, and the precipitate allowed to settle for several hours. The supernatant was decanted and discarded; then the wash procedure was repeated until the supernatant was colorless, approximately two to three times. The precipitate was collected on a scintered glass funnel, washed with methanol and air dried overnight. On some occasions, the precipitate was collected by centrifugation at 5000 rpm for 10 minutes before washing with methanol and air drying overnight. The dried mannan powder was dissolved in distilled waster, using approximately 5 ml water per gram of dry mannan powder. The final concentration of *S. uvarum* cell wall mannan was approximately 30 µg/ml.

B. Preparation of *S. uvarum* Mannan ELISA Plates

*S. uvarum* cell mannan ELISA plates were saturated with antigen as follows. Purified *S. uvarum* mannan prepared as described above was diluted to a concentration of 100 µg/ml with phosphate buffered saline/0.2% sodium azide (PBS-N3). Using a multi-channel pipettor, 100 µl of 100 µg/ml *S. uvarum* mannan was added per well of a Costar 96-well hi-binding plate (catalogue number 3590; Costar Corp., Cambridge, Mass.). The antigen was allowed to coat the plate at 4° C. for a minimum of 12 hours. Each lot of plates was compared to a previous lot before use. Plates were stored at 2-8° C. for up to one month.

C. Analysis of Patient Sera

Patient sera were analyzed in duplicate for anti-IgG or anti-IgA reactivity. Microtiter plates saturated with antigen as described above were incubated with phosphate buffered saline/0.05% Tween-20 for 45 minutes at room temperature to inhibit nonspecific antibody binding. Patient sera were subsequently added at a dilution of 1:80 and incubated for 1 hour at room temperature. Wells were washed three times with PBS/0.05% Tween-20. Then a 1:1000 dilution of alkaline phosphatase-conjugated goat anti-human F(ab') fragment-specific IgG (Pierce, Rockford, Ill.) or alpha chain-specific IgA (Jackson Immunoresearch Labs, Inc., West Grove, Pa.) was added, and the microtiter plates incubated for 1 hour at room temperature. After washing, a solution of p-nitrophenol phosphate in diethanolamine substrate buffer was added, and color development allowed to proceed for 10 minutes. Absorbance at 405 nm with a reference wavelength of 650 nm was analyzed using an automated EMAX plate reader (Molecular Devices, Menlo Park, Calif.).

Standard binding of pooled sera from patients with an established diagnosis of Crohn's disease was used as a standard reference for binding and set to be 100 ELISA units. Results with test patient sera were expressed as a percentage of the standard binding of the reference Crohn's disease sera. Sera showing ASCA reactivity (IgG, IgA, or both) exceeding the reference range were termed ASCA positive.

EXAMPLE IV

Genotyping for Three Crohn's Disease Associated Variants of NOD2

This example shows a genotyping assay that can be used to detect the presence or absence of a NOD2 variant.

Genotyping was performed using a genotyping assay employing 5'-exonuclease technology, the TaqMan MGB™ assay (PE Biosystems; Foster City, Calif.). Primers were designed using the software PrimerExpress 1.5™ (PE Biosystems) and sequence information found in dbSNP for NOD2 variants R702W, G908R, and 1007fs. The MGB™ design adds a "minor groove binder" to the 3' end of the TaqMan™ probes, thereby increasing the binding temperature of the probe and enabling the use of shorter probes than in conventional TaqMan™ assays (Kutyavin et al., *Nucleic Acids Res.* 25:3718-3723 (1997)). This has the effect of increasing the discrimination between the alleles in the assay (Kutyavin et al., *Nucleic Acids Res.* 28:655-661 (2000)). Assays were performed following the manufacturer's recommendations (PE Biosystems bulletin 4317594) in an ABI 7900 instrument. Genotyping was performed blinded to clinical status of the subjects. Primers and probes used in the genotyping assay are shown in Tables 1 and 2.

TABLE 1

Primers Used in Taqman MGB™ Assay for NOD2 Variants

| Primer | Forward Primer | SNP Reverse Primer | SEQ ID NO |
|---|---|---|---|
| R702W | 5'CTGGCTGAGTGCCA GACATCT 3' | 5'GGCGGGATGGAGTGGA A 3' | for 11 rev 12 |
| G908R | 5'CCACCTCAAGCTCT GGTGATC 3' | 5'GTTGACTCTTTTGGCC TTTTCAG 3' | for 13 rev 14 |
| 1007fs | 5'CCTTACCAGACTTC CAGGATGGT 3' | 5'TGTCCAATAACTGCAT CACCTACCT 3' | for 15 rev 16 |

TABLE 2

TAQMAN PROBES

| Allele detected | Probe sequence | Seq ID NO |
|---|---|---|
| R702W wild type allele | 6FAM-TGCTCCGGCGCCA-MGBNFQ | 17 |
| R702W variant allele | TET-CTGCTCTGGCGCCA-MGBNFQ | 18 |
| G908R wild type allele | 6FAM-CTCTGTTGCCCCAGAA-MGBNFQ | 19 |
| G908R variant allele | TET-CTCTGTTGCGCCAGA-MGBNFQ | 20 |
| 1007fs wild type allele | TET-CTTTCAAGGGCCTGC-MGBNFQ | 21 |
| 1007fs variant allele ("2") | 6FAM-CCTTTCAAGGGGCCT-MGBNFQ | 22 |

EXAMPLE V

Anti-IgA OmpC ELISA

This example describes an ELISA for direct detection of IgA anti-OmpC antibodies in patient sera.

A. ELISA

The OmpC direct ELISA is performed as follows. Plates (Greiner, USA Scientific, Ocala, Fla.) are coated overnight at 4° C. with 100 µl/well OmpC prepared as described below at 0.25 µg/ml in borate buffered saline, pH 8.5. After three washes in 0.05% Tween 20 in phosphate buffered saline (PBS), the plates are blocked with 150 µl/well of 0.5% bovine serum albumin in PBS, pH 7.4 (BSA-PBS) for 30 minutes at room temperature. The blocking solution is then replaced with 100 µl/well of Crohn's disease or normal control serum, diluted 1:100. The plates are then incubated for 2 hours at room temperature and washed as before. Alkaline phosphatase conjugated goat anti-human IgA (α-chain specific), or IgG (γ chain specific) (Jackson ImmunoResearch, West Grove, Pa.) is added to the plates at a dilution of 1:1000 in BSA-PBS. The plates are incubated for 2 hours at room temperature before washing three times with 0.05% Tween 20/PBS followed by another three washes with Tris buffered normal saline, pH 7.5. Substrate solution (1.5 mg/ml disodium p-nitrophenol phosphate (Aresco; Solon, Ohio) in 2.5 mM $MgCl_2$, 0.01 M Tris, pH 8.6) is added at 100 µl/well, and color allowed to develop for one hour. The plates are then analyzed at 405 nm.

IgA OmpC positive reactivity is defined as reactivity greater than two standard deviations above the mean reactivity obtained with control (normal) sera analyzed at the same time as the test samples.

B. Purification of OmpC

The protocol below describes purification of OmpC using spheroplast lysis.

OmpF$^{-/-}$/OmpA$^{-/-}$ mutant *E. coli* are inoculated from a glycerol stock into 10-20 ml of Luria Bertani broth supplemented with 100 µg/ml streptomycin (LB-Strep, Teknova, Half Moon Bay, Calif.), and cultured vigorously at 37° C. for about 8 hours to log phase, followed by expansion to 1 liter in LB-Strep over 15 hours at 25° C.

The cells are harvested by centrifugation (JS-4.2, 4K/15 min/4° C.). If necessary, cells are washed twice with 100 ml of ice cold 20 mM Tris-Cl pH 7.5. The cells are subsequently resuspended in ice cold spheroplast forming buffer (20 mM Tris-Cl pH 7.5, 20% sucrose, 0.1 M EDTA pH 8.0, 1 mg/ml lysozyme), after which the resuspended cells are incubated on ice for about 1 hour with occasional mixing by inversion.

If required, the spheroplasts are centrifuged (JA-17, 5.5 k/10 min/4° C.) and resuspended in a smaller volume of spheroplast forming buffer (SFB). The spheroplast pellet is optionally frozen prior to resuspension in order to improve lysis efficiency. Hypotonic buffer is avoided in order to avoid bursting the spheroplasts and releasing chromosomal DNA, which significantly decreases the efficiency of lysis.

The spheroplast preparation is diluted 14-fold into ice cold 10 mM Tris-Cl pH 7.5, 1 mg/ml DNase-I, and vortexed vigorously. The preparation is sonicated on ice 4×30 seconds at 50% power at setting 4, with a pulse "On time" of 1 second, without foaming or overheating the sample.

Cell debris is pelleted by centrifugation (JA-17, 5-10K/10 min/4° C.), and the supernatant removed and clarified by centrifugation a second time (10K/10 min/4° C.). The supernatant is removed without collecting any part of the pellet, and placed into ultra centrifuge tubes. The tubes are filled to 115 millimeter from top with 20 mM Tris-Cl pH 7.5.

The membrane preparation is pelleted by ultra centrifugation at 100,000 g (35K/1 hour/4° C. in Beckman SW 60 swing bucket rotor). The pellet is resuspended by homogenizing into 20 mM Tris-Cl pH 7.5 using a 1 ml blue pipette tip and squirting the pellet closely before pipetting up and down for approximately 10 minutes per tube.

In a 15 ml screw cap tube filled with 4 mls, the material is extracted for 1 hour in 20 mM Tris-Cl pH 7.5 with 1% SDS, with rotation at 37° C. The preparation is transferred to ultra centrifugation tubes, and the membrane pelleted at 100,000 g (35K/1 hour/4° C. in Beckman SW 60). The pellet is resuspended by homogenizing into 20 mM Tris-Cl pH 7.5 as before. The membrane preparation is optionally left at 4° C. overnight.

OmpC is extracted for 1 hour with rotation at 37° C. in 20 mM Tris-Cl pH 7.5, 3% SDS, and 0.5 M NaCl (SDS will precipitate if kept below 37° C.). The material is transferred to ultra centrifugation tubes, and the membrane pelleted by centrifugation at 100,000 g (35K/1 hour/30° C. in Beckman SW 60). Lower temperatures are avoided since further cooling will result in extracted protein salting out of solution.

The supernatant containing extracted OmpC is then dialyzed against more than 10,000 volumes to eliminate high salt content. SDS is removed by detergent exchange against 0.2% Triton. Triton is removed by further dialysis against 50 mM Tris-Cl.

Purified OmpC, which functions as a porin in its trimeric form, is characterized as follows when analyzed by SDS-PAGE. Electrophoresis at room temperature results in a ladder of about 100 kDa, about 70 kDa, and about 30 kDa bands. Heating for 10-15 minutes at 65-70° C. partially dissociates the complex and results in only dimers and monomers (about 70 kDa and about 30 kDa bands). Boiling for 5 minutes results in monomers of 38 kDa.

EXAMPLE VI

ELISA and Indirect Immunofluorescence for Determining pANCA Status

This example describes methods for determining the pANCA status of a subject.

A. Presence of pANCA is Determined by Fixed Neutrophil ELISA

A fixed neutrophil enzyme-linked immunosorbent assay is used to detect pANCA as described in Saxon et al., *J. Allergy Clin. Immunol.* 86:202-210 (1990), and all samples are analyzed in a blinded fashion. Microtiter plates are coated with 2.5×10⁵ neutrophils per well and treated with 100% methanol to fix the cells. Cells are incubated with 0.25% bovine serum albumin (BSA) in phosphate-buffered saline to block nonspecific antibody binding. Next, control and coded sera are added at a 1:100 dilution to the bovine serum/phosphate-buffered saline blocking buffer. Alkaline phosphatase conjugated goat F(ab')$_2$ anti-human immunoglobulin G (γ-chain specific) antibody (Jackson Immunoresearch Labs, Inc., West Grove, Pa.) is added at a 1:1000 dilution to label neutrophil bound antibody. A p-nitrophenol phosphate substrate solution is added and color development is allowed to proceed until absorbance at 405 nm in the positive control wells is 0.8-1.0 optical density units greater than the absorbance in blank wells.

Levels are determined relative to a standard consisting of pooled sera obtained from well-characterized pANCA positive ulcerative colitis patients. Results are expressed as ELISA units. Sera with circulating antineutrophil cytoplasmic IgG antibody exceeding the reference range value are termed ANCA positive. Numerical values that are below the reference range are termed ANCA negative.

B. Indirect Immunofluorescence Assay for Determination of ANCA Staining Pattern

Indirect immunofluorescent staining is performed on samples that are ANCA-positive by ELISA to determine whether the predominant staining pattern is perinuclear (pANCA) or cytoplasmic (cANCA). Glass slides containing approximately 100,000 neutrophils per slide are prepared by cytocentrifugation (Shandon Cytospin, Cheshire, England) and they are fixed in 100% methanol, air-dried, and stored at −20° C. The fixed neutrophils are incubated with human sera are diluted (1:20), and the reaction is visualized with fluorescein-labeled F(ab')$_2$ γ chain-specific antibody as described in Saxon et al., supra, 1990. The slides are examined using an epifluorescence-equipped Olympus BH-2 microscope (Olympus, Lake Success, N.Y.).

pANCA positivity is defined as a perinuclear staining pattern combined with ELISA reactivity greater than two standard deviations above the mean reactivity obtained with control (normal) sera analyzed at the same time as the test samples.

All journal article, reference and patent citations provided herein, including referenced sequence accession numbers of nucleotide and amino acid sequences contained in various databases, in parentheses or otherwise, whether previously stated or not, are incorporated herein by reference in their entirety.

Although the invention has been described with reference to the disclosed embodiments, those skilled in the art will readily appreciate that the specific experiments detailed are only illustrative of the invention. It should be understood that various modifications can be made without departing from the spirit of the invention.

---

We claim:

1. A method for determining the likelihood of being susceptible to a fibrostenotic subtype of Crohn's disease characterized by small bowel involvement in a subject having Crohn's disease, said method comprising:
   (a) contacting a sample obtained from the subject with an antigen or fragment thereof specifically reactive with IgA anti-I2 antibodies; and
   (b) measuring the level of IgA anti-I2 antibodies in said sample with an enzyme linked immunosorbent assay (ELISA) to detect specific binding of said IgA anti-I2 antibodies to said antigen or fragment thereof, wherein a high level of said IgA anti-I2 antibodies is indicative of an increased likelihood of said fibrostenotic subtype of Crohn's disease characterized by small bowel involvement.

2. The method of claim 1, wherein said ELISA comprises the steps of:
   (a) contacting a sample obtained from the subject with an I2 antigen under conditions suitable to form a first complex of I2 antigen and antibody against said I2 antigen;
   (b) contacting said first complex with a labeled secondary antibody to form a second complex; and
   (c) detecting a level of said second complex, wherein a high level of said second complex indicates a high level of said IgA anti-I2 antibodies in the subject.

3. The method of claim 1, further comprising determining the presence or absence of a NOD2 variant selected from the group consisting of SEQ ID NO: 3, SEQ ID NO: 4, SEQ ID NO: 5, SEQ ID NO: 6, SEQ ID NO: 7, and SEQ ID NO: 8 in the subject, wherein a high level of IgA anti-I2 antibodies and the presence of said NOD2 variant in the subject indicates an increased likelihood of an aggressive form of said fibrostenotic subtype of Crohn's disease requiring small bowel surgery.

4. The method of claim 3, wherein the combined high level of said IgA anti-I2 antibodies and the presence of said NOD2 variant in the subject indicates an increased likelihood of an aggressive form of said fibrostenotic subtype of Crohn's disease requiring small bowel surgery with an odds ratio of at least 6.

5. The method of claim 1, further comprising determining the level of anti-*Saccharomyces cerevisiae* antibodies (ASCA) in the subject, comprising contacting a sample obtained from the subject with an antigen or fragment thereof specifically reactive with ASCA; and measuring the level of ASCA in said sample by detecting specific binding of said ASCA to said antigen or fragment thereof, wherein a high level of said IgA anti-I2 antibodies and a high level of said ASCA in the subject indicates an increased likelihood of an aggressive form of said fibrostenotic subtype of Crohn's disease requiring small bowel surgery.

6. The method of claim 5, wherein the combined high levels of said IgA anti-I2 antibodies and said ASCA in the subject indicates an increased likelihood of an aggressive form of said fibrostenotic subtype of Crohn's disease requiring small bowel surgery with an odds ratio of at least 6.

7. The method of claim 3, further comprising determining the level of said ASCA in the subject, comprising contacting a sample obtained from the subject with an antigen or fragment thereof specifically reactive with ASCA; and measuring the level of ASCA in said sample to detect specific binding of said ASCA to said antigen or fragment thereof, wherein the combined high levels of IgA anti-I2 antibodies and said ASCA and the presence of said NOD2 variant in the subject indicates the greatest likelihood for an aggressive form of said fibrostenotic subtype of Crohn's disease requiring small bowel surgery.

8. The method of claim 7, wherein the combined high levels of said IgA anti-I2 antibodies and said ASCA and the presence of said NOD2 variant in the subject indicates an increased likelihood of an aggressive form of said fibrostenotic subtype of Crohn's disease requiring small bowel surgery with an odds ratio of at least 9.

9. The method of claim 1, wherein said antigen comprises an I2 antigen or fragment thereof.

10. The method of claim 9, wherein said I2 antigen comprises a GST-I2 antigen or fragment thereof.

11. The method of claim 2, wherein the labeled secondary antibody comprises a label selected from the group consisting of horseradish peroxidase (HRP), alkaline phosphatase (AP), β-galactosidase, and urease.

12. A method for determining the likelihood of being susceptible to a fibrostenotic subtype of Crohn's disease characterized by small bowel involvement in a subject having Crohn's disease, said method comprising:
(a) contacting a sample obtained from the subject with an antigen or fragment thereof specifically reactive with IgA anti-I2 antibodies; and
(b) measuring the level of IgA anti-I2 antibodies in said sample with an enzyme linked immunosorbent assay (ELISA) to detect specific binding of said IgA anti-I2 antibodies to said antigen or fragment thereof,
wherein a high level of said IgA anti-I2 antibodies is indicative of an increased likelihood of the fibrostenotic subtype of Crohn's disease characterized by small bowel involvement, and wherein said fibrostenotic subtype is further characterized by the absence of features of ulcerative colitis.

13. The method of claim 12, further comprising determining the presence or absence of a NOD2 variant selected from the group consisting of SEQ ID NO: 3, SEQ ID NO: 4, SEQ ID NO: 5, SEQ ID NO: 6, SEQ ID NO: 7, and SEQ ID NO: 8, and determining the level in the subject of one or more markers selected from the group consisting of anti-*Saccharomyces cerevisiae* antibodies (ASCA), IgA anti-OmpC antibodies, and perinuclear anti-neutrophil cytoplasmic antibodies (pANCA), wherein the level of each of said one or more markers is determined by contacting the sample with an antigen or fragment thereof specifically reactive with each of the one or more markers, and measuring the level of each of said one or more markers by detecting specific binding of each of said one or more markers to said antigen or fragment thereof.

14. The method of claim 13, wherein said one or more markers is ASCA.

15. The method of claim 12, wherein said ELISA comprises the steps of:
(a) contacting a sample obtained from the subject with an I2 antigen under conditions suitable to form a first complex of I2 antigen and antibody against said I2 antigen;
(b) contacting said first complex with a labeled secondary antibody to form a second complex; and
(c) detecting a level of said second complex, wherein a high level of said second complex indicates a high level of said IgA anti-I2 antibodies in the subject.

16. The method of claim 12, wherein said antigen comprises an I2 antigen or fragment thereof.

17. The method of claim 16, wherein said I2 antigen comprises a GST-I2 antigen or fragment thereof.

18. The method of claim 15, wherein the labeled secondary antibody comprises a label selected from the group consisting of horseradish peroxidase (HRP), alkaline phosphatase (AP), β-galactosidase, and urease.

19. A method for determining the likelihood of being susceptible to a clinical subtype of Crohn's disease characterized by the need for small bowel surgery in a subject having Crohn's disease, said method comprising:
(a) contacting a sample obtained from the subject with an antigen or fragment thereof specifically reactive with IgA anti-I2 antibodies, and
(b) measuring the level of IgA anti-I2 antibodies in said sample with an enzyme linked immunosorbent assay (ELISA) to detect specific binding of said IgA anti-I2 antibodies to said antigen or fragment thereof,
wherein a high level of said IgA anti-I2 antibodies is indicative of an increased likelihood of the clinical subtype of Crohn's disease characterized by the need for small bowel surgery.

20. The method of claim 19, further comprising determining the presence or absence of a NOD2 variant selected from the group consisting of SEQ ID NO: 3, SEQ ID NO: 4, SEQ ID NO: 5, SEQ ID NO: 6, SEQ ID NO: 7, and SEQ ID NO: 8, and determining the level in the subject of one or more markers selected from the group consisting of anti-*Saccharomyces cerevisiae* antibodies (ASCA), IgA anti-OmpC antibodies, and perinuclear anti-neutrophil cytoplasmic antibodies (pANCA), wherein the level of each of said one or more markers is determined by contacting the sample with an antigen or fragment thereof specifically reactive with each of the one or more markers, and measuring the level of each of said one or more markers by detecting specific binding of each of said one or more markers to said antigen or fragment thereof.

21. The method of claim 20, wherein said one or more markers is ASCA.

22. The method of claim 19, wherein said ELISA comprises the steps of:
(a) contacting a sample obtained from the subject with an I2 antigen under conditions suitable to form a first complex of I2 antigen and antibody against said I2 antigen;
(b) contacting said first complex with a labeled secondary antibody to form a second complex; and
(c) detecting a level of said second complex, wherein a high level of said second complex indicates a high level of said IgA anti-I2 antibodies in the subject.

23. The method of claim 19, wherein said antigen comprises an I2 antigen or fragment thereof.

24. The method of claim 23, wherein said I2 antigen comprises a GST-I2 antigen or fragment thereof.

25. The method of claim 22, wherein the labeled secondary antibody comprises a label selected from the group consisting of horseradish peroxidase (HRP), alkaline phosphatase (AP), β-galactosidase, and urease.

26. A method for determining the likelihood of being susceptible to a clinical subtype of Crohn's disease characterized by the absence of features of ulcerative colitis in a subject having Crohn's disease, said method comprising:
  (a) contacting a sample obtained from the subject with an antigen or fragment thereof specifically reactive with IgA anti-I2 antibodies, and
  (b) measuring the level of IgA anti-I2 antibodies in said sample with an enzyme linked immunosorbent assay (ELISA) to detect specific binding of said IgA anti-I2 antibodies to said antigen or fragment thereof,
  wherein a high level of said IgA anti-I2 antibodies is indicative of an increased likelihood of the clinical subtype of Crohn's disease characterized by the absence of features of ulcerative colitis.

27. The method of claim 26, further comprising determining the presence or absence of a NOD2 variant selected from the group consisting of SEQ ID NO: 3, SEQ ID NO: 4, SEQ ID NO: 5, SEQ ID NO: 6, SEQ ID NO: 7, and SEQ ID NO: 8, and determining the level in the subject of one or more markers selected from the group consisting of anti-*Saccharomyces cerevisiae* antibodies (ASCA), IgA anti-OmpC antibodies, and perinuclear anti-neutrophil cytoplasmic antibodies (pANCA), wherein the level of each of said one or more markers is determined by contacting the sample with an antigen or fragment thereof specifically reactive with each of the one or more markers, and measuring the level of each of said one or more markers by detecting specific binding of each of said one or more markers to said antigen or fragment thereof.

28. The method of claim 27, wherein said one or more markers is ASCA.

29. The method of claim 26, wherein said ELISA comprises the steps of:
  (a) contacting a sample obtained from the subject with an I2 antigen under conditions suitable to form a first complex of I2 antigen and antibody against said I2 antigen;
  (b) contacting said first complex with a labeled secondary antibody to form a second complex; and
  (c) detecting a level of said second complex, wherein a high level of said second complex indicates a high level of said IgA anti-I2 antibodies in the subject.

30. The method of claim 26, wherein said antigen comprises an I2 antigen or fragment thereof.

31. The method of claim 30, wherein said I2 antigen comprises a GST-I2 antigen or fragment thereof.

32. The method of claim 29, wherein the labeled secondary antibody comprises a label selected from the group consisting of horseradish peroxidase (HRP), alkaline phosphatase (AP), β-galactosidase, and urease.

* * * * *

UNITED STATES PATENT AND TRADEMARK OFFICE
CERTIFICATE OF CORRECTION

PATENT NO. : 8,163,501 B2  
APPLICATION NO. : 12/645394  
DATED : April 24, 2012  
INVENTOR(S) : Stephan R. Targan et al.

Page 1 of 1

It is certified that error appears in the above-identified patent and that said Letters Patent is hereby corrected as shown below:

In the Specification

Column 1, Line 6: Please delete "grant number DK 46763" and insert in its place --Grant No. DK046763--; please delete "the".

Column 1, Line 7: Please delete "United States Government" and insert in its place --government--.

Column 1, Line 8: Please delete "this" and insert in its place --the--.

Signed and Sealed this  
Ninth Day of May, 2017

Michelle K. Lee  
*Director of the United States Patent and Trademark Office*

SEQUENCE LISTING

```
<160> NUMBER OF SEQ ID NOS: 22

<210> SEQ ID NO 1
<211> LENGTH: 302
<212> TYPE: DNA
<213> ORGANISM: Pseudomonas aeruginosa
<220> FEATURE:
<221> NAME/KEY: CDS
<222> LOCATION: (2)...(301)
<223> OTHER INFORMATION: T cell superantigen I2, PfI2, microbial
      homologue PA2885, pfiT, putative repressor of atu genes (atuR)

<400> SEQUENCE: 1 a gat ctg gcc agc gcc gtg ggc atc cag tcc ggc agc atc ttt cat cac      49
  Asp Leu Ala Ser Ala Val Gly Ile Gln Ser Gly Ser Ile Phe His His
   1               5                  10                  15 ttc aag agc aag gat gag ata ttg cgt gcc gtg atg gag gaa acc atc       97
Phe Lys Ser Lys Asp Glu Ile Leu Arg Ala Val Met Glu Glu Thr Ile
             20                  25                  30 cat tac aac acc gcg atg atg cgc gct tca ctg gag gag gcg agc acg      145
His Tyr Asn Thr Ala Met Met Arg Ala Ser Leu Glu Glu Ala Ser Thr
         35                  40                  45 gtg cgc gaa cgc gtg ctg gcg ctg atc cgc tgc gag ttg cag tcg atc      193
Val Arg Glu Arg Val Leu Ala Leu Ile Arg Cys Glu Leu Gln Ser Ile
     50                  55                  60 atg ggc ggc agt ggc gag gcc atg gcg gtg ctg gtc tac gaa tgg cgc      241
Met Gly Gly Ser Gly Glu Ala Met Ala Val Leu Val Tyr Glu Trp Arg
 65                  70                  75                  80 tcg ctg tcg gcc gaa ggc cag gcg cac gtg ctg gcc ctg cgt gac gtg      289
Ser Leu Ser Ala Glu Gly Gln Ala His Val Leu Ala Leu Arg Asp Val
                 85                  90                  95
```

```
tat gag cag atc t                                              302
Tyr Glu Gln Ile
        100

<210> SEQ ID NO 2
<211> LENGTH: 100
<212> TYPE: PRT
<213> ORGANISM: Pseudomonas aeruginosa
<220> FEATURE:
<223> OTHER INFORMATION: T cell superantigen I2, PfI2, microbial
      homologue PA2885, pfiT, putative repressor of atu genes (atuR)

<400> SEQUENCE: 2

Asp Leu Ala Ser Ala Val Gly Ile Gln Ser Gly Ser Ile Phe His His
 1               5                  10                  15

Phe Lys Ser Lys Asp Glu Ile Leu Arg Ala Val Met Glu Glu Thr Ile
            20                  25                  30

His Tyr Asn Thr Ala Met Met Arg Ala Ser Leu Glu Glu Ala Ser Thr
        35                  40                  45

Val Arg Glu Arg Val Leu Ala Leu Ile Arg Cys Glu Leu Gln Ser Ile
    50                  55                  60

Met Gly Gly Ser Gly Glu Ala Met Ala Val Leu Val Tyr Glu Trp Arg
65                  70                  75                  80

Ser Leu Ser Ala Glu Gly Gln Ala His Val Leu Ala Leu Arg Asp Val
                85                  90                  95

Tyr Glu Gln Ile
        100

<210> SEQ ID NO 3
<211> LENGTH: 494
<212> TYPE: DNA
<213> ORGANISM: Homo sapiens
<220> FEATURE:
<223> OTHER INFORMATION: nucleotide sequence of NOD2 gene surrounding
      R702W SNP variant, Hugot R675W, SNP 8 allele, "2" allele at SNP8,
      rs2066844

<400> SEQUENCE: 3
accttcagat cacagcagcc ttcctggcag ggctgttgtc ccgggagcac tggggcctgc    60
tggctgagtg ccagacatct gagaaggccc tgctccggcg ccaggcctgt gcccgctggt   120
gtctggcccg cagcctccgc aagcacttcc actccatccc gccagctgca ccgggtgagg   180
ccaagagcgt gcatgccatg cccgggttca tctggctcat ccggagcctg tacgagatgc   240
aggaggagcg gctggctcgg aaggctgcac gtggcctgaa tgttgggcac ctcaagttga   300
cattttgcag tgtgggcccc actgagtgtg ctgccctggc ctttgtgctg cagcacctcc   360
ggcggcccgt ggccctgcag ctggactaca actctgtggg tgacattggc ctggagcagc   420
tgctgccttg ccttggtgtc tgcaaggctc tgtagtgagt gttactgggc attgctgttc   480
aggtatgggg gagc                                                    494

<210> SEQ ID NO 4
<211> LENGTH: 494
<212> TYPE: DNA
<213> ORGANISM: Homo sapiens
<220> FEATURE:
<223> OTHER INFORMATION: complement of nucleotide sequence of NOD2 gene
      surrounding R702W SNP variant, Hugot R675W, SNP 8 allele, "2"
      allele at SNP8, rs2066844

<400> SEQUENCE: 4
gctcccccat acctgaacag caatgcccag taacactcac tacagagcct tgcagacacc    60
```

```
aaggcaaggc agcagctgct ccaggccaat gtcacccaca gagttgtagt ccagctgcag    120
ggccacgggc cgccggaggt gctgcagcac aaaggccagg gcagcacact cagtggggcc    180
cacactgcaa aatgtcaact tgaggtgccc aacattcagg ccacgtgcag ccttccgagc    240
cagccgctcc tcctgcatct cgtacaggct ccggatgagc cagatgaacc cgggcatggc    300
atgcacgctc ttggcctcac ccggtgcagc tggcgggatg gagtggaagt gcttgcggag    360
gctgcgggcc agacaccagc gggcacaggc ctggcgccgg agcagggcct tctcagatgt    420
ctggcactca gccagcaggc cccagtgctc ccgggacaac agccctgcca ggaaggctgc    480
tgtgatctga aggt                                                     494
```

```
<210> SEQ ID NO 5
<211> LENGTH: 540
<212> TYPE: DNA
<213> ORGANISM: Homo sapiens
<220> FEATURE:
<223> OTHER INFORMATION: nucleotide sequence of NOD2 gene surrounding
      G908R SNP variant, Hugot G881R, SNP 12 allele, "2" allele at
      SNP12, rs2066845

<400> SEQUENCE: 5
```

```
atcaaaaccc tgagaggaca agggacattt ccaagtcacc cagaaagact cgagtgtcct     60
ctcttgaaat ccaatggtct ttttccttta ctccattgcc taacattgtg gggtagaaat    120
aaagttcaaa gaccttcaga actggcccca gctcctccct cttcacctga tctccccaag    180
aaaactgcag gatagactct gaagcttacc tgagccacct caagctctgg tgatcaccca    240
aggcttcagc cagggcctgg gccccctcgt cacccactct gttgccccag aatctgaaaa    300
ggccaaaaga gtcaacagac agtgtcagtg agtacctgat atgtgttcta gacatgaact    360
aacagtcctc ctccctctgc agtcccagcc agaggggcag gaccactcaa tcccagagtg    420
gcctcactgg ggctcctggt cccagcaaag tggacctgcc tccatctttt gggtgggatg    480
gccaaactta acccaagagt tttcagtggc tttacattac agacttagag aatagtagag    540
```

```
<210> SEQ ID NO 6
<211> LENGTH: 540
<212> TYPE: DNA
<213> ORGANISM: Homo sapiens
<220> FEATURE:
<223> OTHER INFORMATION: complement of nucleotide sequence of NOD2 gene
      surrounding G908R SNP variant, Hugot G881R, SNP 12 allele, "2"
      allele at SNP12, rs2066845

<400> SEQUENCE: 6
```

```
ctctactatt ctctaagtct gtaatgtaaa gccactgaaa actcttgggt taagtttggc     60
catcccaccc aaaagatgga ggcaggtcca ctttgctggg accaggagcc ccagtgaggc    120
cactctggga ttgagtggtc ctgcccctct ggctgggact gcagagggag gaggactgtt    180
agttcatgtc tagaacacat atcaggtact cactgacact gtctgttgac tcttttggcc    240
ttttcagatt ctggggcaac agagtgggtg acgagggggc ccaggccctg gctgaagcct    300
tgggtgatca ccagagcttg aggtggctca ggtaagcttc agagtctatc ctgcagtttt    360
cttggggaga tcaggtgaag agggaggagc tggggccagt tctgaaggtc tttgaacttt    420
atttctaccc cacaatgtta ggcaatggag taaggaaaaa agaccattgg atttcaagag    480
aggacactcg agtctttctg ggtgacttgg aaatgtccct tgtcctctca gggttttgat    540
```

```
<210> SEQ ID NO 7
<211> LENGTH: 541
<212> TYPE: DNA
```

<213> ORGANISM: Homo sapiens
<220> FEATURE:
<223> OTHER INFORMATION: nucleotide sequence of NOD2 gene surrounding
      1007fs SNP variant, frame shift insertion mutation, Hugot 3020insC
      or 980fs, SNP 13 allele, "2" allele at SNP13, rs2066847

<400> SEQUENCE: 7

```
tttaaaaatg aaatcattgc tccctactta aagaggtaaa gacttctttc ttagacagag    60
aatcagatcc ttcacatgca gaatcattct cactgaatgt cagaatcaga agggatcctc   120
aaaattctgc cattcctctc tcccgtcacc ccattttaca gatagaaaaa ctgaggttcg   180
gagagctaaa acaggcctgc caggggcct taccagactt ccaggatggt gtcattcctt    240
tcaaggggcc tgcaggaggg cttctgcccc taggtaggtg atgcagttat ggacaacct    300
ggaaaagaag atacaatggt gagcttcaag gattcttggt tttcctcttg aaactgtcca   360
gttaaagaga ctgcaggagt tagccagtct actgaagccc acctgtccct tagacacatc   420
ctgctcatgt ctgagattcc caatgagctc atcaacaaag gctcagtacc atcagtgaaa   480
tgtaaccgtc tctcttccat tcactagatg agtttatcaa attaagtagc cactccctta   540
g                                                                   541
```

<210> SEQ ID NO 8
<211> LENGTH: 541
<212> TYPE: DNA
<213> ORGANISM: Homo sapiens
<220> FEATURE:
<223> OTHER INFORMATION: complement of nucleotide sequence of NOD2 gene
      surrounding 1007fs SNP variant, frame shift insertion mutation,
      Hugot 3020insC or 980fs, SNP 13 allele, "2" allele at SNP13,
      rs2066847

<400> SEQUENCE: 8

```
ctaagggagt ggctacttaa tttgataaac tcatctagtg aatggaagag agacggttac    60
atttcactga tggtactgag cctttgttga tgagctcatt gggaatctca gacatgagca   120
ggatgtgtct aagggacagg tgggcttcag tagactggct aactcctgca gtctctttaa   180
ctggacagtt tcaagaggaa aaccaagaat ccttgaagct caccattgta tcttcttttc   240
caggttgtcc ataactgca tcacctacct aggggcagaa gccctcctgc aggcccttg     300
aaaggaatga caccatcctg gaagtctggt aaggcccctg gcaggcctg ttttagctct    360
ccgaacctca gttttctat ctgtaaaatg gggtgacggg agagaggaat ggcagaattt    420
tgaggatccc ttctgattct gacattcagt gagaatgatt ctgcatgtga aggatctgat   480
tctctgtcta agaaagaagt ctttacctct ttaagtaggg agcaatgatt tcattttaa    540
a                                                                   541
```

<210> SEQ ID NO 9
<211> LENGTH: 1101
<212> TYPE: DNA
<213> ORGANISM: Escherichia coli
<220> FEATURE:
<223> OTHER INFORMATION: E. coli K-12, strain W620 outer membrane
      protein c (OmpC) precursor, pro-OmpC, pheS
<220> FEATURE:
<221> NAME/KEY: CDS
<222> LOCATION: (1)...(1101)
<223> OTHER INFORMATION: outer membrane protein c (OmpC) precursor,
      pro-OmpC, pheS

<400> SEQUENCE: 9

```
atg aaa gtt aaa gta ctg tcc ctc ctg gtc cca gct ctg ctg gta gca    48
Met Lys Val Lys Val Leu Ser Leu Leu Val Pro Ala Leu Leu Val Ala
1               5                   10                  15
```

```
ggc gca gca aac gct gct gaa gtt tac aac aaa gac ggc aac aaa tta      96
Gly Ala Ala Asn Ala Ala Glu Val Tyr Asn Lys Asp Gly Asn Lys Leu
                 20                  25                  30 gat ctg tac ggt aaa gta gac ggc ctg cac tat ttc tct gac aac aaa     144
Asp Leu Tyr Gly Lys Val Asp Gly Leu His Tyr Phe Ser Asp Asn Lys
         35                  40                  45 gat gta gat ggc gac cag acc tac atg cgt ctt ggc ttc aaa ggt gaa     192
Asp Val Asp Gly Asp Gln Thr Tyr Met Arg Leu Gly Phe Lys Gly Glu
 50                  55                  60 act cag gtt act gac cag ctg acc ggt tac ggc cag tgg gaa tat cag     240
Thr Gln Val Thr Asp Gln Leu Thr Gly Tyr Gly Gln Trp Glu Tyr Gln
 65                  70                  75                  80 atc cag ggc aac agc gct gaa aac gaa aac aac tcc tgg acc cgt gtg     288
Ile Gln Gly Asn Ser Ala Glu Asn Glu Asn Asn Ser Trp Thr Arg Val
                 85                  90                  95 gca ttc gca ggt ctg aaa ttc cag gat gtg ggt tct ttc gac tac ggt     336
Ala Phe Ala Gly Leu Lys Phe Gln Asp Val Gly Ser Phe Asp Tyr Gly
            100                 105                 110 cgt aac tac ggc gtt gtt tat gac gta act tcc tgg acc gac gta ctg     384
Arg Asn Tyr Gly Val Val Tyr Asp Val Thr Ser Trp Thr Asp Val Leu
        115                 120                 125 cca gaa ttc ggt ggt gac acc tac ggt tct gac aac ttc atg cag cag     432
Pro Glu Phe Gly Gly Asp Thr Tyr Gly Ser Asp Asn Phe Met Gln Gln
130                 135                 140 cgt ggt aac ggc ttc gcg acc tac cgt aac act gac ttc ttc ggt ctg     480
Arg Gly Asn Gly Phe Ala Thr Tyr Arg Asn Thr Asp Phe Phe Gly Leu
145                 150                 155                 160 gtt gac ggc ctg aac ttt gct gtt cag tac cag ggt aaa aac ggc aac     528
Val Asp Gly Leu Asn Phe Ala Val Gln Tyr Gln Gly Lys Asn Gly Asn
                165                 170                 175 cca tct ggt gaa ggc ttt act agt ggc gta act aac aac ggt cgt gac     576
Pro Ser Gly Glu Gly Phe Thr Ser Gly Val Thr Asn Asn Gly Arg Asp
            180                 185                 190 gca ctg cgt caa aac ggc gac ggc gtc ggc ggt tct atc act tat gat     624
Ala Leu Arg Gln Asn Gly Asp Gly Val Gly Gly Ser Ile Thr Tyr Asp
        195                 200                 205 tac gaa ggt ttc ggt atc ggt ggt gcg atc tcc agc tcc aaa cgt act     672
Tyr Glu Gly Phe Gly Ile Gly Gly Ala Ile Ser Ser Ser Lys Arg Thr
    210                 215                 220 gat gct cag aac acc gct gct tac atc ggt aac ggc gac cgt gct gaa     720
Asp Ala Gln Asn Thr Ala Ala Tyr Ile Gly Asn Gly Asp Arg Ala Glu
225                 230                 235                 240 acc tac act ggt ggt ctg aaa tac gac gct aac aac atc tac ctg gct     768
Thr Tyr Thr Gly Gly Leu Lys Tyr Asp Ala Asn Asn Ile Tyr Leu Ala
                245                 250                 255 gct cag tac acc cag acc tac aac gca act cgc gta ggt tcc ctg ggt     816
Ala Gln Tyr Thr Gln Thr Tyr Asn Ala Thr Arg Val Gly Ser Leu Gly
            260                 265                 270 tgg gcg aac aaa gca cag aac ttc gaa gct gtt gct cag tac cag ttc     864
Trp Ala Asn Lys Ala Gln Asn Phe Glu Ala Val Ala Gln Tyr Gln Phe
        275                 280                 285 gac ttc ggt ctg cgt ccg tcc ctg gct tac ctg cag tct aaa ggt aaa     912
Asp Phe Gly Leu Arg Pro Ser Leu Ala Tyr Leu Gln Ser Lys Gly Lys
    290                 295                 300 aac ctg ggt cgt ggc tac gac gac gaa gat atc ctg aaa tat gtt gat     960
Asn Leu Gly Arg Gly Tyr Asp Asp Glu Asp Ile Leu Lys Tyr Val Asp
305                 310                 315                 320 gtt ggt gct acc tac tac ttc aac aaa aac atg tcc acc tac gtt gac    1008
Val Gly Ala Thr Tyr Tyr Phe Asn Lys Asn Met Ser Thr Tyr Val Asp
                325                 330                 335
```

```
tac aaa atc aac ctg ctg gac gac aac cag ttc act cgt gac gct ggc    1056
Tyr Lys Ile Asn Leu Leu Asp Asp Asn Gln Phe Thr Arg Asp Ala Gly
            340                 345                 350 atc aac act gat aac atc gta gct ctg ggt ctg gtt tac cag ttc        1101
Ile Asn Thr Asp Asn Ile Val Ala Leu Gly Leu Val Tyr Gln Phe
            355                 360                 365

<210> SEQ ID NO 10
<211> LENGTH: 367
<212> TYPE: PRT
<213> ORGANISM: Escherichia coli
<220> FEATURE:
<223> OTHER INFORMATION: E. coli K-12, strain W620 outer membrane
      protein c (OmpC) precursor, pro-OmpC

<400> SEQUENCE: 10

Met Lys Val Lys Val Leu Ser Leu Leu Val Pro Ala Leu Leu Val Ala
 1               5                   10                  15

Gly Ala Ala Asn Ala Ala Glu Val Tyr Asn Lys Asp Gly Asn Lys Leu
            20                  25                  30

Asp Leu Tyr Gly Lys Val Asp Gly Leu His Tyr Phe Ser Asp Asn Lys
        35                  40                  45

Asp Val Asp Gly Asp Gln Thr Tyr Met Arg Leu Gly Phe Lys Gly Glu
    50                  55                  60

Thr Gln Val Thr Asp Gln Leu Thr Gly Tyr Gly Gln Trp Glu Tyr Gln
65                  70                  75                  80

Ile Gln Gly Asn Ser Ala Glu Asn Glu Asn Asn Ser Trp Thr Arg Val
                85                  90                  95

Ala Phe Ala Gly Leu Lys Phe Gln Asp Val Gly Ser Phe Asp Tyr Gly
            100                 105                 110

Arg Asn Tyr Gly Val Val Tyr Asp Val Thr Ser Trp Thr Asp Val Leu
        115                 120                 125

Pro Glu Phe Gly Gly Asp Thr Tyr Gly Ser Asp Asn Phe Met Gln Gln
    130                 135                 140

Arg Gly Asn Gly Phe Ala Thr Tyr Arg Asn Thr Asp Phe Phe Gly Leu
145                 150                 155                 160

Val Asp Gly Leu Asn Phe Ala Val Gln Tyr Gln Gly Lys Asn Gly Asn
                165                 170                 175

Pro Ser Gly Glu Gly Phe Thr Ser Gly Val Thr Asn Asn Gly Arg Asp
            180                 185                 190

Ala Leu Arg Gln Asn Gly Asp Gly Val Gly Gly Ser Ile Thr Tyr Asp
        195                 200                 205

Tyr Glu Gly Phe Gly Ile Gly Gly Ala Ile Ser Ser Ser Lys Arg Thr
    210                 215                 220

Asp Ala Gln Asn Thr Ala Ala Tyr Ile Gly Asn Gly Asp Arg Ala Glu
225                 230                 235                 240

Thr Tyr Thr Gly Gly Leu Lys Tyr Asp Ala Asn Asn Ile Tyr Leu Ala
                245                 250                 255

Ala Gln Tyr Thr Gln Thr Tyr Asn Ala Thr Arg Val Gly Ser Leu Gly
            260                 265                 270

Trp Ala Asn Lys Ala Gln Asn Phe Glu Ala Val Ala Gln Tyr Gln Phe
        275                 280                 285

Asp Phe Gly Leu Arg Pro Ser Leu Ala Tyr Leu Gln Ser Lys Gly Lys
    290                 295                 300

Asn Leu Gly Arg Gly Tyr Asp Asp Glu Asp Ile Leu Lys Tyr Val Asp
305                 310                 315                 320
```

-continued

```
Val Gly Ala Thr Tyr Tyr Phe Asn Lys Asn Met Ser Thr Tyr Val Asp
            325                 330                 335

Tyr Lys Ile Asn Leu Leu Asp Asp Asn Gln Phe Thr Arg Asp Ala Gly
        340                 345                 350

Ile Asn Thr Asp Asn Ile Val Ala Leu Gly Leu Val Tyr Gln Phe
    355                 360                 365

<210> SEQ ID NO 11
<211> LENGTH: 21
<212> TYPE: DNA
<213> ORGANISM: Artificial Sequence
<220> FEATURE:
<223> OTHER INFORMATION: synthetic SNP forward primer R702W used in
      Taqman MGB assay for NOD2 variants

<400> SEQUENCE: 11
ctggctgagt gccagacatc t                                          21

<210> SEQ ID NO 12
<211> LENGTH: 17
<212> TYPE: DNA
<213> ORGANISM: Artificial Sequence
<220> FEATURE:
<223> OTHER INFORMATION: synthetic SNP reverse primer R702W used in
      Taqman MGB assay for NOD2 variants

<400> SEQUENCE: 12
ggcgggatgg agtggaa                                               17

<210> SEQ ID NO 13
<211> LENGTH: 21
<212> TYPE: DNA
<213> ORGANISM: Artificial Sequence
<220> FEATURE:
<223> OTHER INFORMATION: synthetic SNP forward primer G908R used in
      Taqman MGB assay for NOD2 variants

<400> SEQUENCE: 13
ccacctcaag ctctggtgat c                                          21

<210> SEQ ID NO 14
<211> LENGTH: 23
<212> TYPE: DNA
<213> ORGANISM: Artificial Sequence
<220> FEATURE:
<223> OTHER INFORMATION: synthetic SNP reverse primer G908R used in
      Taqman MGB assay for NOD2 variants

<400> SEQUENCE: 14
gttgactctt ttggccttttt cag                                       23

<210> SEQ ID NO 15
<211> LENGTH: 23
<212> TYPE: DNA
<213> ORGANISM: Artificial Sequence
<220> FEATURE:
<223> OTHER INFORMATION: synthetic SNP forward primer 1007fs used in
      Taqman MGB assay for NOD2 variants

<400> SEQUENCE: 15
ccttaccaga cttccaggat ggt                                        23

<210> SEQ ID NO 16
<211> LENGTH: 25
<212> TYPE: DNA
<213> ORGANISM: Artificial Sequence
<220> FEATURE:
```

<223> OTHER INFORMATION: synthetic SNP reverse primer 1007fs used in
      Taqman MGB assay for NOD2 variants

<400> SEQUENCE: 16
tgtccaataa ctgcatcacc tacct                                         25

<210> SEQ ID NO 17
<211> LENGTH: 13
<212> TYPE: DNA
<213> ORGANISM: Artificial Sequence
<220> FEATURE:
<223> OTHER INFORMATION: synthetic Taqman probe for detection of R702W
      wild type allele
<221> NAME/KEY: modified_base
<222> LOCATION: (1)...(1)
<223> OTHER INFORMATION: t modified by fluorescent reporter dye 6FAM
<221> NAME/KEY: modified_base
<222> LOCATION: (13)...(13)
<223> OTHER INFORMATION: a modified by quencher dye DNA minor groove
      binder (MGB) MGBNFQ

<400> SEQUENCE: 17
tgctccggcg cca                                                      13

<210> SEQ ID NO 18
<211> LENGTH: 14
<212> TYPE: DNA
<213> ORGANISM: Artificial Sequence
<220> FEATURE:
<223> OTHER INFORMATION: synthetic Taqman probe for detection of R702W
      variant allele
<221> NAME/KEY: modified_base
<222> LOCATION: (1)...(1)
<223> OTHER INFORMATION: c modified by fluorescent reporter dye TET
<221> NAME/KEY: modified_base
<222> LOCATION: (14)...(14)
<223> OTHER INFORMATION: a modified by quencher dye DNA minor groove
      binder (MGB) MGBNFQ

<400> SEQUENCE: 18
ctgctctggc gcca                                                     14

<210> SEQ ID NO 19
<211> LENGTH: 16
<212> TYPE: DNA
<213> ORGANISM: Artificial Sequence
<220> FEATURE:
<223> OTHER INFORMATION: synthetic Taqman probe for detection of G908R
      wild type allele
<221> NAME/KEY: modified_base
<222> LOCATION: (1)...(1)
<223> OTHER INFORMATION: c modified by fluorescent reporter dye 6FAM
<221> NAME/KEY: modified_base
<222> LOCATION: (16)...(16)
<223> OTHER INFORMATION: a modified by quencher dye DNA minor groove
      binder (MGB) MGBNFQ

<400> SEQUENCE: 19
ctctgttgcc ccagaa                                                   16

<210> SEQ ID NO 20
<211> LENGTH: 15
<212> TYPE: DNA
<213> ORGANISM: Artificial Sequence
<220> FEATURE:
<223> OTHER INFORMATION: synthetic Taqman probe for detection of G908R
      variant allele
<221> NAME/KEY: modified_base
<222> LOCATION: (1)...(1)
<223> OTHER INFORMATION: c modified by fluorescent reporter dye TET
<221> NAME/KEY: modified_base
<222> LOCATION: (15)...(15)

-continued

```
<223> OTHER INFORMATION: a modified by quencher dye DNA minor groove
      binder (MGB) MGBNFQ

<400> SEQUENCE: 20
ctctgttgcg ccaga                                                     15

<210> SEQ ID NO 21
<211> LENGTH: 15
<212> TYPE: DNA
<213> ORGANISM: Artificial Sequence
<220> FEATURE:
<223> OTHER INFORMATION: synthetic Taqman probe for detection of 1007fs
      wild type allele
<221> NAME/KEY: modified_base
<222> LOCATION: (1)...(1)
<223> OTHER INFORMATION: c modified by fluorescent reporter dye TET
<221> NAME/KEY: modified_base
<222> LOCATION: (15)...(15)
<223> OTHER INFORMATION: c modified by quencher dye DNA minor groove
      binder (MGB) MGBNFQ

<400> SEQUENCE: 21
ctttcaaggg cctgc                                                     15

<210> SEQ ID NO 22
<211> LENGTH: 15
<212> TYPE: DNA
<213> ORGANISM: Artificial Sequence
<220> FEATURE:
<223> OTHER INFORMATION: synthetic Taqman probe for detection of 1007fs
      variant allele
<221> NAME/KEY: modified_base
<222> LOCATION: (1)...(1)
<223> OTHER INFORMATION: c modified by fluorescent reporter dye 6FAM
<221> NAME/KEY: modified_base
<222> LOCATION: (15)...(15)
<223> OTHER INFORMATION: t modified by quencher dye DNA minor groove
      binder (MGB) MGBNFQ

<400> SEQUENCE: 22
cctttcaagg ggcct                                                     15
```